US009075903B2

(12) United States Patent
Marshall et al.

(10) Patent No.: US 9,075,903 B2
(45) Date of Patent: Jul. 7, 2015

(54) USER INTERFACE FOR MEDICAL IMAGE REVIEW WORKSTATION

(75) Inventors: Julian Marshall, Los Altos, CA (US); Brian T. Matuska, Stockton, CA (US); Chinghsiang Chang, Sunnyvale, CA (US); Edgar W. Chen, Fremont, CA (US)

(73) Assignee: HOLOGIC, INC., Marlborough, MA (US)

( * ) Notice: Subject to any disclaimer, the term of this patent is extended or adjusted under 35 U.S.C. 154(b) by 712 days.

(21) Appl. No.: 13/302,465

(22) Filed: Nov. 22, 2011

(65) Prior Publication Data

US 2012/0133601 A1 May 31, 2012

Related U.S. Application Data

(60) Provisional application No. 61/417,394, filed on Nov. 26, 2010.

(51) Int. Cl.
*G06F 3/048* (2013.01)
*G06F 19/00* (2011.01)

(52) U.S. Cl.
CPC .......... *G06F 19/3406* (2013.01); *G06F 19/321* (2013.01)

(58) Field of Classification Search
CPC ............................... G06F 3/048; G06F 3/0482
USPC ......................................................... 345/173
See application file for complete search history.

(56) References Cited

U.S. PATENT DOCUMENTS

| | | | |
|---|---|---|---|
| 6,901,156 B2 | 5/2005 | Giger et al. | |
| 7,022,075 B2 | 4/2006 | Grunwald et al. | |
| 7,289,825 B2 | 10/2007 | Fors et al. | |
| 7,406,150 B2 | 7/2008 | Minyard et al. | |
| 7,705,830 B2 | 4/2010 | Westerman et al. | |
| 7,809,175 B2 | 10/2010 | Roehrig et al. | |
| 7,828,733 B2 | 11/2010 | Zhang et al. | |
| 7,974,924 B2 | 7/2011 | Holla et al. | |
| 8,677,282 B2 * | 3/2014 | Cragun et al. | 715/863 |
| 2002/0188466 A1 | 12/2002 | Barrette et al. | |
| 2003/0048260 A1 | 3/2003 | Matusis | |
| 2006/0098855 A1 | 5/2006 | Gkanatsios et al. | |
| 2007/0046649 A1 | 3/2007 | Reiner | |
| 2007/0118400 A1 | 5/2007 | Morita et al. | |
| 2008/0114614 A1 | 5/2008 | Mahesh et al. | |

(Continued)

OTHER PUBLICATIONS

International Search Report mailed Mar. 22, 2012, in corresponding International Application No. PCT/US2011/061875, filed Nov. 22, 2011.

(Continued)

*Primary Examiner* — Quan-Zhen Wang
*Assistant Examiner* — David Lee
(74) *Attorney, Agent, or Firm* — Vista IP Law Group LLP

(57) ABSTRACT

Methods, systems and computer program products for controlling display of different types of medical images and providing touchscreen interfaces for display on a mobile communication device and associated with different image types, e.g., different imaging modalities or different view modes. Detection of a multi-finger tap on the screen of the mobile communication device while viewing a first touchscreen interface for an image type invokes a second or auxiliary touchscreen interface for that image type having a subset of interface elements of the first touchscreen interface.

11 Claims, 18 Drawing Sheets

(56) References Cited

U.S. PATENT DOCUMENTS

| | | | |
|---|---|---|---|
| 2008/0125643 A1 | 5/2008 | Huisman | |
| 2008/0165136 A1 | 7/2008 | Christie et al. | |
| 2008/0240533 A1 | 10/2008 | Piron et al. | |
| 2008/0297482 A1* | 12/2008 | Weiss | 345/173 |
| 2009/0129644 A1 | 5/2009 | Daw et al. | |
| 2009/0167702 A1 | 7/2009 | Nurmi | |
| 2010/0079405 A1* | 4/2010 | Bernstein | 345/174 |
| 2010/0088346 A1 | 4/2010 | Urness et al. | |
| 2010/0131294 A1 | 5/2010 | Venon et al. | |
| 2010/0131482 A1 | 5/2010 | Linthicum et al. | |
| 2010/0259561 A1 | 10/2010 | Forutanpour et al. | |
| 2010/0260316 A1 | 10/2010 | Stein et al. | |
| 2011/0105879 A1 | 5/2011 | Masumoto | |
| 2011/0310126 A1* | 12/2011 | Georgiev et al. | 345/660 |
| 2012/0131488 A1* | 5/2012 | Karlsson et al. | 715/771 |
| 2012/0133600 A1 | 5/2012 | Marshall et al. | |

OTHER PUBLICATIONS

Written Opinion mailed Mar. 22, 2012, in corresponding International Application No. PCT/US2011/061875, filed Nov. 22, 2011.

Office Action Dated Oct. 1, 2013, in corresponding U.S. Appl. No. 13/302,277, filed Nov. 22, 2011 36 pages.

"Now Playing: Radiology Images from Your Hospital PACS on your iPad," Felasfa Wodajo, MD, Mar. 17, 2010; web site: http://www.imedicalapps.com/2010/03/now-playing-radiology-images-from-your-hospital-pacs-on-your-ipad/, accessed on Nov. 31, 2011 (3 pages).

eFilm Mobile HD by Merge Healthcare, web site: http://itunes.apple.com/bw/app/efilm-mobile-hd/id405261243?mt=8, accessed on Nov. 31, 2011 (2 pages).

eFilm Solutions, eFilm Workstation (tm) 3.4, website: http://estore.merge.com/na/estore/content.aspx?productID=405, accessed on Nov. 31, 2011 (2 pages).

* cited by examiner

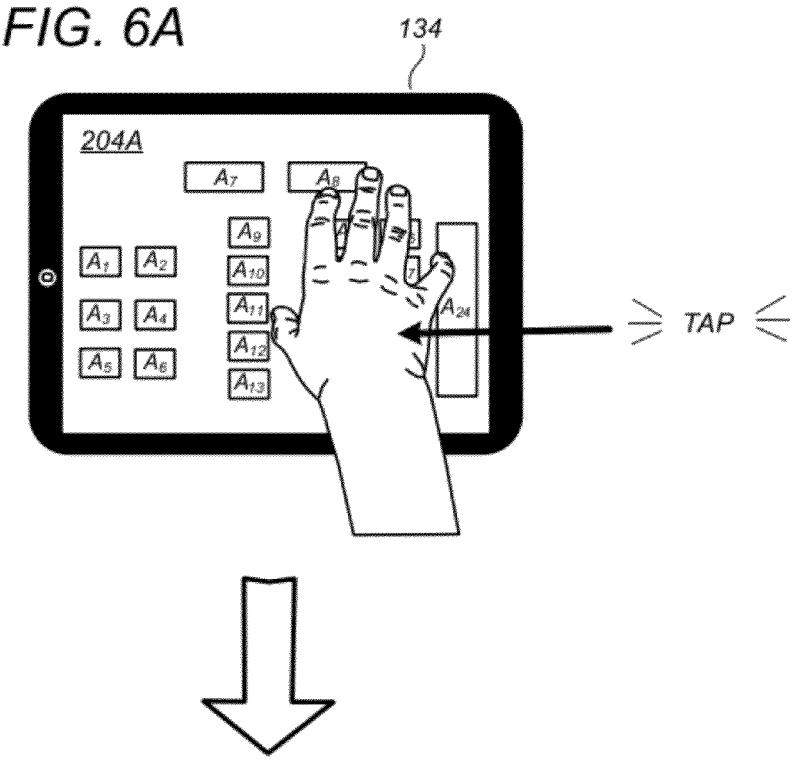
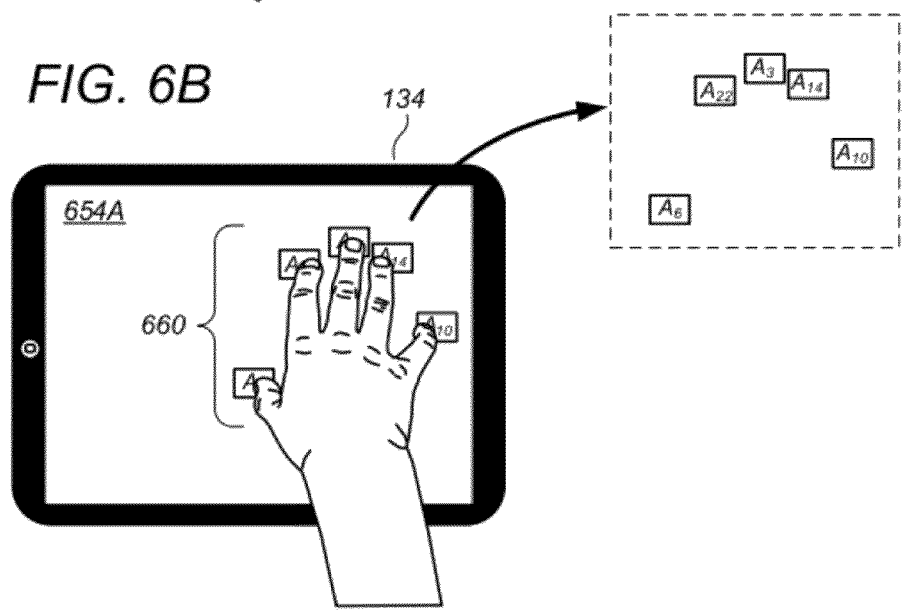

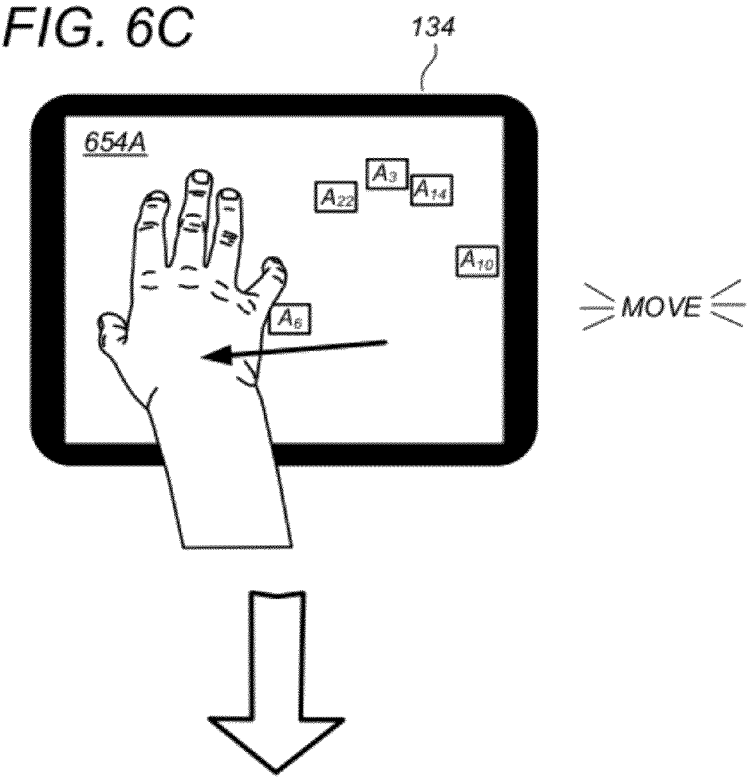
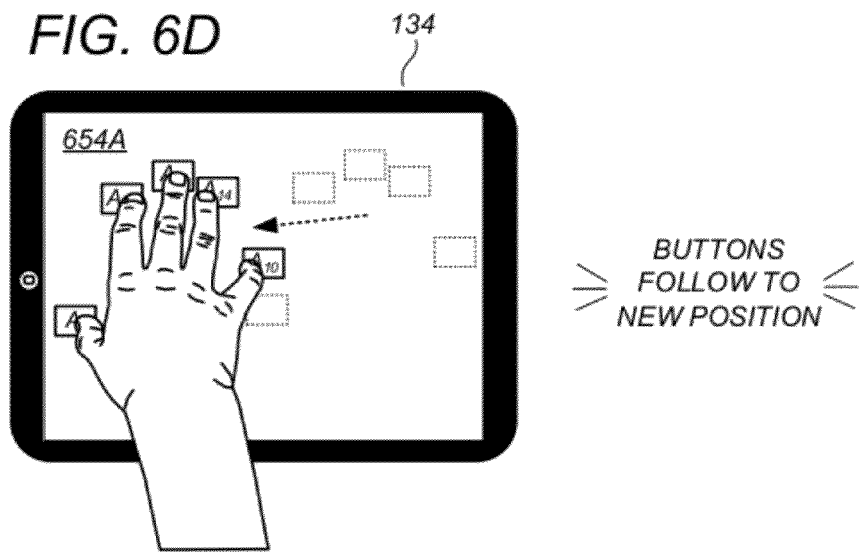

USER INTERFACE FOR MEDICAL IMAGE REVIEW WORKSTATION

CROSS-REFERENCE TO RELATED APPLICATION

This application claims priority under 35 U.S.C. §119 from provisional U.S. Patent Application Ser. No. 61/417,394, filed Nov. 26, 2010, the contents of which are incorporated hereby by reference as though set forth in full.

FIELD

This patent specification relates to medical imaging. More particularly, this patent specification relates to user interfaces for medical image review workstations.

BACKGROUND

Substantial effort and attention has been directed to increasing the capabilities of medical imaging systems, including continued research and development into new medical imaging modalities, the ongoing improvement of existing imaging modalities, and the expansion of data processing, presentation, and storage capabilities for ensuring the beneficial use of the acquired medical image data for the ultimate goal of improving overall patient health. One particularly crucial component of the medical imaging environment is the medical image review workstation, which is where all of the specially acquired and processed image information is presented to a radiologist so that critical health-related decisions can be made. As used herein, radiologist generically refers to a medical professional that analyzes medical images and makes clinical determinations therefrom, it being understood that such person or user of the review workstation might be titled differently, or might have differing qualifications, depending on the country or locality of their particular medical environment.

In association with the ongoing expansion of medical imaging, data processing, and data storage capabilities, an ever-increasing amount of information is becoming available to the radiologist at the medical image review workstation. Problems can arise, however, at the interface between (a) the amount of information available to the radiologist, and (b) the amount of information that can be usefully accessed and perceived by the radiologist in a reasonable amount of time. These issues are especially important in today's radiology environment, where there is an ongoing tension between providing high-quality detection/diagnosis for each patient and maintaining adequate patient throughput to keep costs under control. A large body of information associated with a patient's medical image data would have substantially diminished value if the radiologist does not have sufficient time, inclination, or information technology (IT) sophistication to properly view that information. It is therefore crucial that the human-machine interface associated with medical image review workstations be as streamlined, appealing, and user-friendly as possible, while also allowing comprehensive access to the large amount of data available.

In addition to human-machine interface capability issues, the ongoing expansion of medical imaging, data processing, and data storage capabilities brings about problems relating to equipment acquisition, maintenance, and upgrade costs for medical image review workstations. As known in the art, it is often the case that medical image review for a particular imaging modality is optimized by the use of an additional hardware user input device other than a conventional keyboard/mouse combination, such as a specialized keypad platform having particular arrangements of buttons, knobs, sliders, joysticks, trackballs, and so forth. Although streamlining the image review process for that particular workstation, these specialized hardware input devices can be disadvantageous in that they add to overall system cost, are usually limited to a single modality, and cannot be easily modified or upgraded. Thus, for example, if it is desired to upgrade to a new software version having different workflow controls, it may be necessary to replace the specialized keypad altogether. As another example, if it is desired to expand the capabilities of the medical image review workstation to include an additional modality (for example, adding an ultrasound review modality to an existing x-ray modality review workstation), then the cost and clutter of a second specialized hardware input device for that additional modality may become necessary.

SUMMARY

Embodiments address shortcomings of known methods and systems by providing a user interface (UI) system for a medical image review workstation that provides a streamlined, appealing, and user-friendly experience for the radiologist. Embodiments also provide such a UI system that is easily and inexpensively upgraded to accommodate new software versions, new capabilities, and/or new imaging modalities for the review workstation. Embodiments also provide such a UI system that is readily personalized and customizable for different users at a single review workstation, and/or readily customizable a single radiologist at multiple different review workstations, and allow for such a UI system to be layered upon existing UI systems without requiring substantial changes to current hardware configurations and without requiring substantial cost investment.

One embodiment is directed a computer-implemented method executed by an interface processor and/or mobile communication device for controlling display of medical images and that comprises establishing a network connection between a mobile communication device and the interface processor operably coupled to a review workstation operable by a user to review medical images using a first UI. The method further comprises determining a first medical image selected by the user (e.g., based on the user highlighting or selecting an image or window containing an image). The first medical image is of a first type, e.g., one or more of being an image of a first imaging modality, a first review mode (e.g., a transverse view mode for a tomosynthesis image), and generated by a first type of imaging device. The method further comprises displaying or invoking for display on a screen of the mobile communication device, a second UI. The second UI comprises a first touchscreen interface for controlling display of the first medical image. The method further comprises determining a second medical image selected by the user, the second medical image is of a second type different than the first type, e.g., one or more of being an image of a second imaging modality, a second review mode (e.g., a transverse mode of a magnetic resonance image rather than a tomosynthesis image, or a single-breast MLO view of an x-ray image a transverse view mode for a tomosynthesis image), and generated by a second type of imaging device. The method further comprises displaying or invoking for display on the screen, a third UI that is also a touchscreen interface but different than the first touchscreen interface, for controlling display of the second medical image.

A further embodiment is directed to a computer-implemented method for controlling display of medical images and that comprises displaying or invoking for display on a screen of a mobile communication device of a user, a first touchscreen interface for controlling display of a selected medical image. The first touchscreen interface has a number of interface elements and is considered to be an initial or primary touchscreen interface. The method further comprises detecting when the user has tapped the screen with a plurality of fingers simultaneously (e.g., with a "five finger tap"). In response to detecting a five finger tap, another touch screen interface is displayed or invoked for display on the mobile communication device screen for controlling display of the selected medical image. According to one embodiment, the second touchscreen interface consists of subset of the plurality of the interface elements of the first touchscreen interface (i.e., the number of elements of the second touchscreen interface is less than the number of elements of the first touchscreen interface). For example, a first or primary touchscreen interface may include interface elements for all available controls, whereas the second or auxiliary touchscreen interface displayed or invoked after a simultaneous finger tap may include only as many interface elements as fingers that tapped the screen simultaneously for selected controls. For example, a first touchscreen UI may include 24 or other numbers of interface elements for various display controls, whereas a second or auxiliary touchscreen interface displayed after a "five finger tap" includes only five interface elements, e.g., five interface elements previously selected by the user, determined to be the most popular or utilized most often, or elements positioned under fingers that tapped the screen.

Yet other embodiments are directed to computer-implemented methods for controlling display of medical images generated by imaging devices of different vendors or manufactures and that may involve different types of interfaces displayed at a review workstation that receives image data from respective different imaging devices. For example, embodiments may involve imaging devices of different manufacturers, which may be of the same imaging modality or different imaging modalities, and that provide different types of interfaces for viewing medical images of the same or different view modes. With embodiments, these different types interfaces can be transformed into corresponding touchscreen interfaces such that a first touchscreen interface is generated, displayed or invoked for display on a screen of a mobile communication device for a first medical image generated by a first imaging device manufactured or sold by a first source, vendor or manufacturer, whereas a second, different touchscreen interface is generated, displayed or invoked for display for a second medical image generated by another imaging device of the same modality (e.g., both imaging devices are tomosynthesis imaging devices), but with a different touchscreen UI. Embodiments allow users to utilize a touchscreen interface displayed on a mobile communication device to control display of medical images, acquired with imaging devices of the same or different manufacturers, which may be of the same or different imaging modalities.

Further embodiments are directed to methods involving how a user of a mobile communication device interacts with and operates touchscreen UIs generated according to embodiments for controlling display of medical images associated with respective view modes and imaging modalities.

Yet other embodiments are directed to articles of manufacture, computer program products and native and downloadable applications executable on a mobile communication device such as a smartphone or tablet computing device capable of wireless communications and configured, operable or programmed to execute methods according to embodiments.

For example, one embodiment is directed to a computer program product, which may comprise a non-transitory computer readable storage medium having stored thereupon a sequence of instructions which, when executed by a computer or mobile communication device, perform a process for controlling display of medical images by displaying or invoking for display on a screen of a mobile communication device a first touchscreen interface for controlling display of the first medical image of a first type, and displaying or invoking for display on the screen, another touchscreen interface different than the first touchscreen interface for controlling display of the second medical image of a second type different than the first type.

As another example, other embodiments are directed to articles of manufacture, computer program products or mobile applications which, when instructions thereof are executed, cause a computer or processing element to perform a process for controlling display of medical images by detecting and responding to a multi-finger or multi-digit tap (e.g., a "five finger tap") by the user on a screen of the mobile communication device. Thus, for example, a first touchscreen interface for controlling display of a selected medical image may be displayed on the screen and includes a plurality of interface elements, the user performs a simultaneous "multi-finger" tap, which is detected, and in response, a second touch screen interface is generated and consists of subset of the plurality of the interface elements of the first touchscreen interface. The subset may be selected by the user to provide for customization, or be determined based on criteria such as most frequent use or position of fingers when the screen is tapped.

Embodiments may be part of or executed by a review workstation, which may include a non-touchscreen interface such as a keyboard and mouse, part of or executed by an interface processor operably coupled to or in communication between a review workstation and a mobile communication device, or part of (e.g., a native application) or downloaded to a mobile communication device and executed by a processor or computing element thereof. Touch screen interfaces may be displayed or invoked by components of a mobile communication device and/or an interface processor operable coupled between the mobile communication device and a review workstation. Thus, an application executing on a mobile communication device may perform various processing to determine how a touchscreen interface should be structured and displayed.

Yet further embodiments are directed to systems configured or operable to analyze medical images using different touchscreen interfaces derived from or resulting from transformation of controls of a UI of a review workstation such that different touchscreen interfaces can be generated for different types of images, e.g., images of different imaging modalities, different view modes, and different imaging modalities and review modes.

For example, one embodiment is directed to a system for controlling display of medical images and comprises a review workstation and an interface processor, which may be an integral component of a review workstation or a separate component that can be connected or plugged into the review workstation. According to one embodiment, the review workstation is operated with a first UI controlled with a keyboard, mouse, trackball, joystick or other physical control element physically manipulated and moved by the user to select a first medical image of a first type and control how the first medical image is displayed on a screen of the review workstation. The interface processor, receiving or determining the selected first medical image and review mode and imaging modality thereof, is configured to communicate with a mobile communication device, and display or invoke for display, on a screen of the mobile communication device, a second UI comprising a first touchscreen interface for controlling display of the first medical image. The interface processor also determines when the user has selected another, second medical image of a second type. Selection of another medical image may be done through the first UI of the review workstation or through the first touchscreen interface displayed on the mobile communication device screen (e.g., via a toggle mechanism that allows the user of the mobile communication device to select an image displayed on the screen of the review workstation). The interface processor then displays or invokes for display on the screen, a third UI comprising a second touchscreen interface that is different than the first touchscreen interface for controlling display of the second medical image of the second type.

System embodiments may involve or comprise only a review workstation configured to establish a wireless connection with a mobile communication device and to display or invoke display of touchscreen interfaces, only an interface processor configured to implement embodiments, only a mobile communication device configured to implement embodiments, or a combination of components such as a review workstation and interface processor, an interface processor and mobile communication device, and all of a review workstation, interface processor and mobile communication device.

In a single or multiple embodiments, a medical image may be selected by the user manipulating the first UI of the review workstation or manipulating a touchscreen interface displayed on a mobile communication device, in response to which a touchscreen interface, or different touchscreen interface, is displayed or invoked to control display of the current or selected medical image.

In a single or multiple embodiments, the interface processor and mobile communication device are in communication via a wireless network. For example, a wireless connection can be established by the mobile communication device being placed in communication with a wireless access point that is in communication with a server hosting the interface processor.

In a single or multiple embodiments, the interface processor, or the application executing on the mobile communication device, receives data of the first UI for controlling display of the first selected image of a first type, transforms those controls into a single-handed or dual-handed touchscreen interface for real-time control of display of the first selected image using the mobile communication device, receives data of another type of image selected by the user, and transforms controls of the first UI into a different touchscreen interface for real-time control of display of the other medical image using the mobile communication device. Touchscreen interfaces have different numbers, shapes and/or spatial arrangements of interface elements depending on the type of image, e.g., the review mode, imaging modality and user preferences In a single or multiple embodiments, the medical images are presented within windows of the first UI. For example, an interface with four windows may include four medical images, each of which is associated with respective view modes and/or imaging modalities. Medical images or windows may be generated by the same review workstation, or by different review workstations, e.g., review workstations of different manufacturers, which may involve different interfaces utilized at the review workstation. The interface processor is a part of or in communication with the review workstation such that the interface processor determines which window is identified or selected as an active window, e.g., based on user manipulation of a mouse or keyboard control at the review workstation or by use of a touchscreen interface displayed on the mobile communication device screen, to determine which medical image or window was selected.

In a single or multiple embodiments, the user manipulating of the mobile communication device itself, e.g., in the form of shaking or jiggling the device, may be detected by an application executing on the mobile communication device. In response to detecting this motion, the application may invoke or display a different touchscreen interface for a given medical displayed, a touchscreen interface for a next image to be analyzed is displayed, or a medical image for a new, different patient, e.g., a randomly selected patient or a next patient in a patient list. If the interface or patient data is not available on the mobile communication device, the mobile communication device can communicate with the interface processor in response to detecting the shaking or jiggling motion.

Further, in a single or multiple embodiments, touchscreen interfaces can be translated to different hands of the user. Thus, if a user is holding a mobile communication device with a left hand such that the user's right hand and fingers thereof are in contact with the screen, if the user switches hands, the application detects the switch based on finger placement or arrangements and then displays or invokes for display elements of the touchscreen interface that are flipped for the other hand. Other customization features according to embodiments include touchscreen interfaces being spatially arranged to be customized to respective lengths of respective fingers of the user of the mobile communication device.

In embodiments involving a multi-finger tap, the auxiliary touchscreen interface displayed following the multi-finger tap includes only a subset of the previously displayed or primary touchscreen interface. The number and/or arrangement of auxiliary interface elements may be based at least in part upon the number of fingers that tapped the screen simultaneously, which interface elements were selected by the user, or determined to be utilized most often. For example, if the user tapped the screen with five fingers (defined to include a thumb and four fingers), then the subset consists of five interface elements, which may be displayed at the same locations tapped by respective fingers, and that may be spatially arranged relative to each other in the same manner as the first or primary interface. The subset of interface elements, in their spatial arrangement, can follow the user's hand as it slides or moves across the screen to a different screen location or as finger lengths and/or positions are adjusted. Thus, for example, a user may be viewing a first medical image associated with a first review mode and first imaging modality using a first touchscreen interface (e.g., with 25 or other number of interface elements), perform a five finger tap, in response to which an auxiliary or secondary UI with only 5 elements is displayed, then perform another five finger tap to toggle back to the primary interface. Thus, a multi-finger tap can be used to switch between primary and secondary or auxiliary touchscreen interfaces, or to invoke some other type of action such as switching to display of medical images of another patient.

Other user actions utilized by embodiments include tracking movement or positioning of a pre-determined digit such as the user's thumb such as when a finger contacts or does not contact (is lifted from) the screen, to then display or invoke a new touchscreen interface, and then displaying or invoking the first or prior touchscreen interface when it is detected that the thumb or other pre-determined finger contacts the screen or has returned to a pre-determined position on the screen.

BRIEF DESCRIPTION OF THE DRAWINGS

FIGS. 3A-B illustrate embodiments involving physical modifications to pre-determined screen locations by application of one or more textured material patches to the screen at locations at which particular touchscreen interface elements are displayed to provide haptic feedback to the user while using the touchscreen interface, wherein FIG. 3A illustrates textured patches applied to the screen, and FIG. 3B illustrates how the spatial arrangement of the applied textured patches shown in FIG. 3A corresponds to particular elements of a touchscreen interface generated according to embodiments;

FIGS. 5A-B illustrate embodiments involving physical modifications to pre-determined screen locations by application templates defining respective voids to the screen such that the voids are at locations at which particular touchscreen interface elements are displayed to provide haptic feedback to the user while using the touchscreen interface, wherein FIG. 5A illustrates the template shown in FIG. 4A applied to the screen to outline groups of elements of a first touchscreen interface, and FIG. 5B illustrates the template shown in FIG. 4B applied to the screen to outline groups of elements of a second touchscreen interface;

FIGS. 6A-D illustrate embodiments involving a multi-finger tap of a screen of a mobile communication device by a user to invoke a touchscreen interface or a change or transformation to a touchscreen interface, wherein FIG. 6A illustrates a first or primary touchscreen user interface as shown in FIG. 2A and including a plurality of interface elements in a particular spatial arrangement and the user performing a multi-finger tap on the screen, FIG. 6B illustrates the resulting second or auxiliary touchscreen interface following the multi-finger tap and that includes only a subset of the interface elements of the first or primary touchscreen user interface, FIG. 6C illustrates the user repositioning a hand after manipulating the second or auxiliary touchscreen user interface shown in FIG. 6B, and FIG. 6D illustrates how the auxiliary touchscreen interface is translated from one hand location to another location or follows the user's hand while maintaining the spatial arrangement of the subset of interface elements to allow the user to manipulate the same auxiliary touchscreen interface at a different screen location;

DETAILED DESCRIPTION OF ILLUSTRATED EMBODIMENTS

Embodiments relate to computer-implemented methods, systems and computer program products or mobile applications for controlling how different types medical images are displayed on a mobile communication device such as a smartphone or tablet computing device capable of wireless communications. With embodiments, a user may utilize touchscreen interfaces that are derived from controls of user interfaces (UIs) of known review workstations, and which can be dynamically adapted in real-time for controlling display of different types of images, e.g., different types of view modes and/or imaging modalities, while the user is holding the mobile communication device. For example, in applications involving analysis of breast tissue, one touchscreen interface may be presented for viewing an image associated with a transverse view mode and an imaging modality of magnetic resonance imaging, whereas another touchscreen interface is generated for viewing the same image but with a different view mode, or for the same view but for an image generated using a different imaging modality. Embodiments also accommodate medical images generated by imaging devices of different manufacturers and respective different interfaces utilized to view images generated by such devices. Various embodiments also provide for the ability to customize touchscreen interfaces.

Certain embodiments are directed to methods, systems and computer program products or mobile applications for determining which images types (of different views and/or acquired with different imaging modalities) are selected by a user with a review workstation UI or a UI displayed on a mobile communication device screen, and displaying or invoking touchscreen interfaces for respective image views and/or images acquired with different imaging modalities. In this manner, a user may manipulate an existing UI of a review workstation, and also manipulate touchscreen interfaces that are adapted or customized for different image views or modalities.

Certain other embodiments are directed to tapping a screen of a mobile communication device with multiple fingers simultaneously (e.g., with five fingers or a thumb and four fingers) to invoke or display an auxiliary UI, which includes only a subset of interface elements, which may be selected by the user or selected as being utilized the most often, of the originally displayed UI, and they can be positioned in the same arrangement as they were in the original UI such that positioning of fingers of the user remains unchanged. In this manner, users can "five finger tap" between the primary or complete UI and one or more auxiliary interfaces. Screen tapping in this manner can also be used to advance to medical images of different patients.

Figure 1:
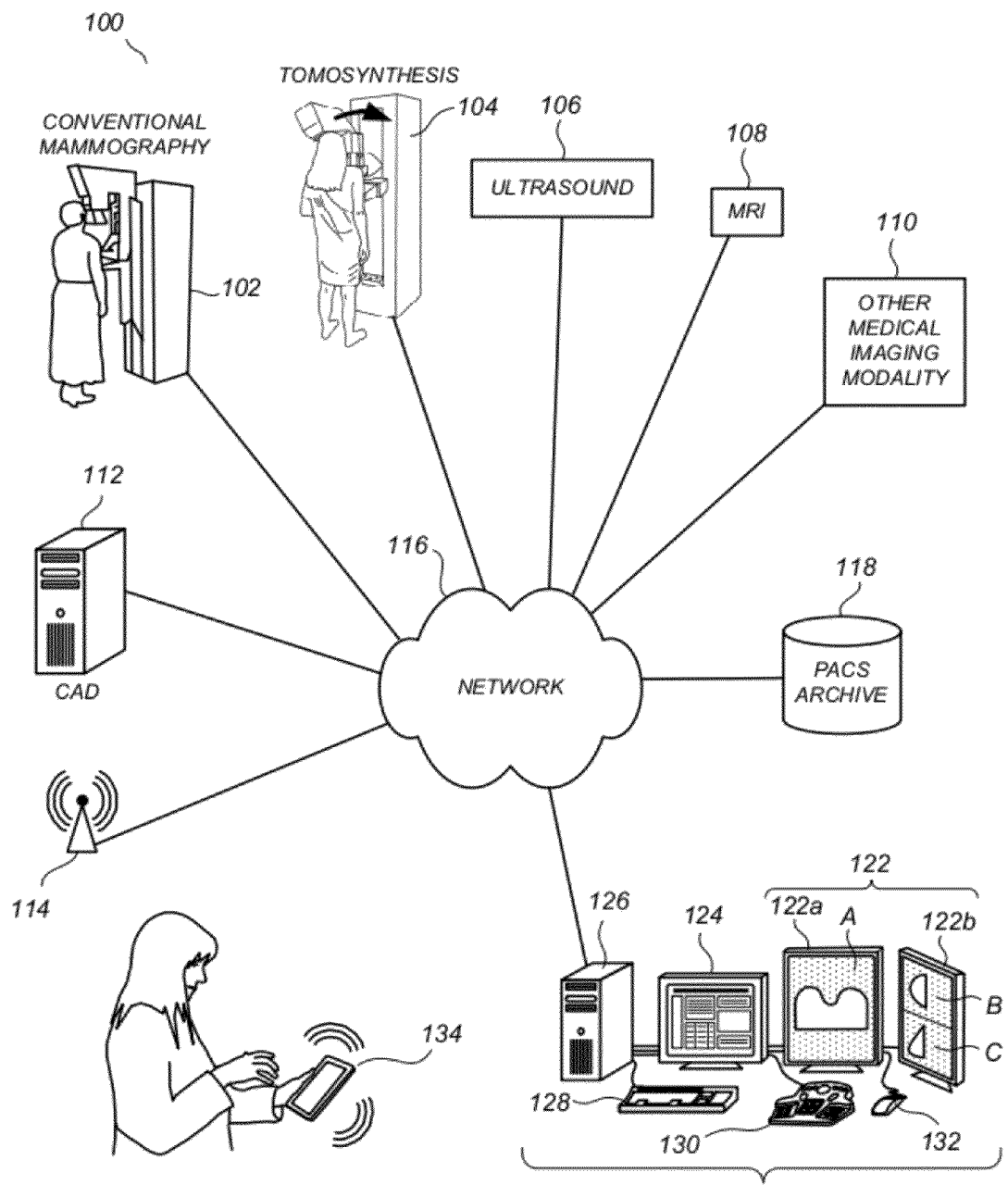
FIG. 1 illustrates an environment including components of one embodiment of a system operable to invoke touchscreen user interfaces on a screen of a mobile communication device adapted for controlling display of different types of medical images, wherein in the illustrated embodiment, an interface processor is operably coupled to a review workstation and in wireless communication with a mobile communication device.

Referring to FIG. 1, a medical imaging environment 100 is illustrated and includes a medical image review workstation or workstation 120 having an enhanced user UI including user control features implemented and/or actuated via a mobile communication device 134 such as a smartphone or tablet computing device capable of wireless communications. Shown in FIG. 1 is a network 116 including a plurality of HIS/RIS (Hospital Information System/Radiology Information System) components coupled thereto, and to which is coupled one or more image acquisition devices examples of which include, but are not limited to, a mammogram acquisition device 102, a tomosynthesis acquisition device 104, an ultrasound acquisition device 106, a magnetic resonance imaging (MRI) acquisition device 108, and a generalized "other" medical imaging device 110 representative of, for example, one or more computerized tomography (CT) imaging or positron emission tomography (PET) acquisition devices.

In the illustrated environment 100, a computer-aided detection (CAD) processor 112 coupled to the network 116 receives digital medical images from one or more of the devices 102, 104, 106, 108, and 110. For tomosynthesis data sets, an additional tomosynthesis reconstruction processor (not shown in FIG. 1) can be coupled to the network 116 to generate and provide a plurality of tomosynthesis reconstructed image slices from x-ray tomosynthesis projection images provided by the tomosynthesis acquisition device 104. The CAD processor 112 processes the medical images according to one or more CAD algorithms and provides CAD findings associated therewith. A UI implemented at the review workstation 120 in conjunction with the mobile communication device 134 interactively displays the medical images to a viewer or user in accordance with one or more of the systems and methods described further hereinbelow. The mobile communication device 134 communicates with the review workstation 120 by virtue of wireless communication (e.g., using the IEEE 802.11 "WiFi" protocol) with wireless access point 114, which is, in turn, connected to the network 116.

Various medical images and related information are communicated according to the DICOM (Digital Imaging and Communications in Medicine) standard and the network 116 supports the TCP/IP protocol, which is used as the transport protocol for the DICOM standard. Also coupled to the network 116 is a PACS archive 118, generally representing a repository for medical information associated with the medical imaging environment, including both current and archived images, current and archived CAD results, radiology reports for completed cases, and so forth. Embodiments described herein can be seamlessly layered upon an existing medical imaging workflow, in which the digital (or digitized) medical images are acquired, optionally processed by the CAD processor 112, and displayed at the review workstation 120 (optionally in conjunction with the associated CAD results) to a radiologist, who makes a clinical determination therefrom.

A UI implemented at the review workstation 120 interactively displays the medical images to a viewer or user (generally, "user") of embodiments in accordance with one or more UI programs carried out on an interface processor 126. Included in conjunction with the UI programs on the interface processor 126 is an auxiliary host application program that, upon execution, communicates with the mobile communication device 134 and carries out the associated functionalities described further herein. Included on the mobile communication device 134 is an auxiliary remote application program that, upon execution, communicates with the auxiliary host application program on the UI processor 126 and carries out the associated functionalities described further herein. The term "server application" can be used interchangeably with "host application" to denote described software that executes on the interface processor 126.

With continuing reference to FIG. 1, a medical imaging environment 100 is illustrated and includes a medical image review workstation 120 having an enhanced UI including user control features implemented and/or actuated via a mobile communication device 134 such as a smartphone, tablet computing device or other mobile communication device 134. Examples of mobile communication devices 134 that may be utilized in embodiments include the IPHONE and IPAD available from Apple, Inc. and other communication or tablet computing device capable of communicating with a review workstation 120 or associated interface processor 126 according to a preferred embodiment.

While it has been found that the IPAD 134 represents one particularly advantageous mobile communication device including hardware, software, network, and development platform for implementing embodiments directed to control of medical image review with UIs described further herein, it is to be appreciated that other known or hereinafter developed mobile communication devices 134 and platforms having generic capabilities analogous to the IPAD 134 can be used in place of an IPAD 134 while remaining within the scope of the preferred embodiments. Preferably, such other known or hereinafter developed mobile communication devices 134 and platforms would include a portable, programmable touchpad computer having a touch-sensitive screen that is of a size and shape to accommodate an open human hand, and would be capable of wireless communication with another computer or network node using Wi-Fi, BLUETOOTH, ZIGBEE, WiMAX, Wireless USB, or any of a host of other standard or non-standard wireless protocols or information transfer modalities (infrared, optical, ultrasonic, etc.). While limiting mobility compared to a wireless connection, embodiments may also involve data connectivity of the portable, programmable touchpad computer through a wired connection, such as wired USB, without necessarily departing from the scope of embodiments. Further, the size of the touchscreen could be made smaller than that of an opened human hand, such as with the touchscreens of IPHONEs or similar portable phones, without necessarily departing from the scope of the present teachings. For ease of explanation, reference is made to an IPAD 134 as a mobile communication device 134 utilized in embodiments, but it will be understood that other mobile communication devices 134 may be utilized, and that such devices may communicate with review workstation 120 or associated interface processor 126.

For convenience of description herein, and without loss of generality, the auxiliary host application program carried out on the UI processor 126 is referred to hereinbelow as the "SVTouch host" or "SVTouch server" program. Further, for convenience and without loss of generality, the auxiliary remote application program carried out on the IPAD 134 is referred to hereinbelow as the "SVTouch remote app."

For purposes of clarity of description, and not by way of limitation, it is disclosed here that SVTouch™ can be seen as being a shorthand term for SECURVIEWTouch™. SECUREVIEW is a registered trademark of Hologic, Inc., of Bedford Mass., where SECURVIEW proprietarily identifies a highly successful and powerful medical image review workstation currently manufactured and sold by Hologic, Inc., the assignee of the present application. SECURVIEW Touch™ proprietarily identifies an extension of the SECURVIEW medical image review workstation that includes one or more aspects of the IPAD-implemented functionality described further herein, which one or more aspects will be publically introduced at the 2010 meeting of the Radiological Society of North America in Chicago, Ill. (RSNA 2010). However, it is to be appreciated that these particular monikers are not used by way of limitation, and that the disclosed systems and methods are applicable across a wide variety of different medical image review workstations from a wide variety of manufacturers, and are further applicable across a wide variety of different touchpad-type platforms other than the IPAD 134.

Review workstation 120 implements an interactive UI using a diagnostic display 122 including first and second display monitors 122a and 122b, an administrative display 124, and user input or control devices including a keyboard 128, a mouse 132, and an application-specific hardware auxiliary input device 130, such as a workflow keypad provided in conjunction with a SECURVIEW medical image review workstation. When the SVTouch host and SVTouch remote applications are activated, the IPAD 134 also becomes part of the UI provided by the review workstation 120. Advantageously, the described SVTouch functionalities can be provided as an add-on that operates side-by-side with the auxiliary hardware input device 130, or alternatively the described SVTouch functionalities can be used to altogether replace the auxiliary input device 130.

Administrative display 124 is used for input and output of a wide variety of information that may be associated with a particular set of medical images (e.g., listings, tables, plots, text descriptions, etc.), as well as for system installation, maintenance, updating, and related tasks. Often provided on the diagnostic display 122 at any particular time during case review by a radiologist are one or more diagnostic images displayed in one or more output windows A, B, and C.

It is to be appreciated that although one or more aspects of the preferred embodiments are described in the particular context of x-ray mammography or x-ray tomosynthesis for single-modality operation, and the contexts of various combinations of x-ray mammography, x-ray tomosynthesis, ultrasound, and MRI for multi-modality operation, embodiments described herein are applicable for a variety of medical imaging modalities in a wide variety of single-modality implementations or multi-modality combinations, such modalities including, but not limited to, two-dimensional x-ray, x-ray tomosynthesis, ultrasound, MRI, CT imaging, PET, single-photon emission computed tomography (SPECT), as well as less conventional medical imaging modalities such as thermography, electrical conductivity-based modalities, and the like. Likewise, although one or more aspects of the preferred embodiments are described in the particular context of breast imaging, the scope of the present teachings extends to medical imaging of any part of the human body including, but not limited to, the prostate, kidneys, other internal organs, head, teeth, neck, abdomen, arms, and other body parts. Examples of medical imaging systems and environments within which one or more aspects of the preferred embodiments are applicable, which includes systems and environments having CAD capability as well as those not having CAD capability, can be found in U.S. Pat. Nos. 6,901,156; 7,406,150; 7,809,175; 7,828,733 and U.S. Publication Nos. 2006/09885; 2008/125643; 2008/0240533 and 2010/260316, each of which is incorporated by reference herein.

Notably, the medical imaging environment 100 of FIG. 1 is presented by way of example only and is not intended to limit the scope of the preferred embodiments to this particular scenario. By way of example, different combinations of the devices 102-132 of FIG. 1 can be placed adjacently to each other or integrated into the same hardware boxes without departing from the scope of the preferred embodiments. By way of still further example, the network 116 can be a wide-area network with the different nodes being distributed throughout a city, a country, or the world. Alternatively, and by way of still further example, some or all of the transfer of digital information among devices 102-132 can be achieved by physical transfer of disks, memory sticks, or other digital media devices without departing from the scope of the preferred embodiments. In view of the present disclosure, a person skilled in the art would be able to implement methods, systems, and/or computer program products capable of achieving the described UIs and processing functionalities without undue experimentation, using publicly available programming tools and software development platforms. By way of example, the SVTouch remote application can be developed using the Objective-C programming language, while the SVTouch host program can be developed using the C# (also termed C-Sharp) programming language.

FIGS. 2A-D illustrate how embodiments are operable transform review workstation 120 UIs into touchscreen user interfaces for a mobile communication device to control display or invoke display of different types of medical images, e.g., medical images of different types of imaging modalities, different types of view modes, or different types of imaging modalities and different types of view modes. Further, embodiments may be operable to control different types of images in that they are generated by the same imaging device, which may generate medical images of the same imaging modality but different review modes, different imaging modalities but the same mode, or different imaging modalities and different respective view modes. Embodiments may also be operable to control display of different types of images generated by imaging devices of different manufacturers, and which may involve different UIs at the review workstation 120.

In the embodiment illustrated in FIGS. 2A-D, the IPAD 134 and the output display 122 of the review workstation 120 while SVTouch host and SVTouch remote applications are running according to a preferred embodiment. The output display 122 currently shows four output windows A, B, C, and D, which either correspond to different types of medical images in that they are of different modalities, or different review modes within a particular modality. As used herein, "active output window" refers to the particular one of the output windows A, B, C, or D to which the radiologist ("user") is focusing their attention, identified or selected. There will generally be no more than one active output window at any particular time.

The identity or selection of the active output window can be established by a variety of different methods, for example, associating the active window with the current location of a cursor 202 or other control or UI element of the review workstation (which does not involve a touchscreen US as in a UI of an IPAD). Thus, when the user hovers the cursor 202 over the "A" output window, such as by controlled movement of the mouse 132, then the "A" window is identified or selected as the active output window. In other embodiments, it can be required that the user provides a mouse click within that output window to establish that output window as the active window, as opposed to merely hovering the mouse over that output window. Alternatively, the active window can be detected by automated head movement detection or automated eye movement detection as used in heads-up displays for fighter aircraft or driver eye activity monitors in newer luxury cars. Any of a variety of other means (direct keyboard input, foot petals, audio inputs) can be used to establish the currently active window without departing from the scope of the present teachings.

Figure 2A:
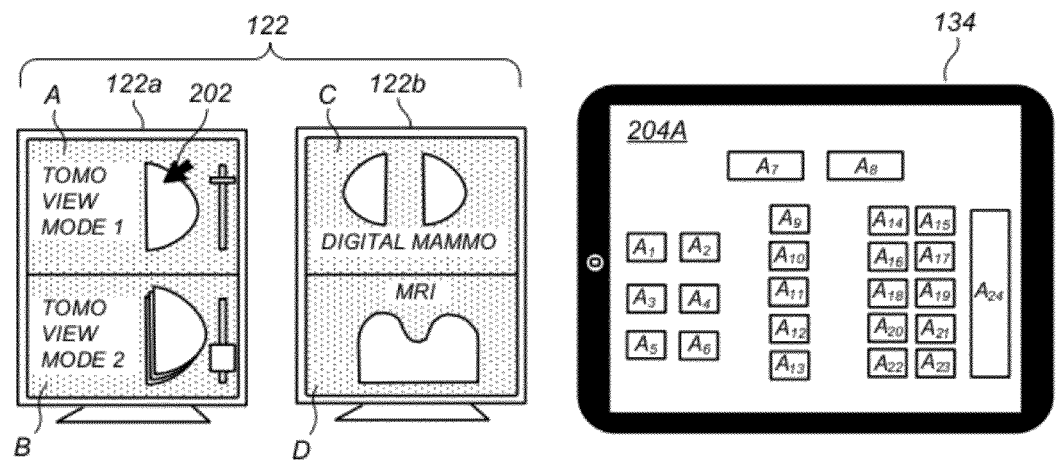
FIGS. 2A-D illustrate examples of output windows of a review workstation and identification or selection of an output window as an active window and respective touchscreen interfaces having respective interface elements configured according to respective spatial arrangements, and displayed or invoked for display on a screen of a mobile communication device to control display of different types of medical images.
Figure 2B:
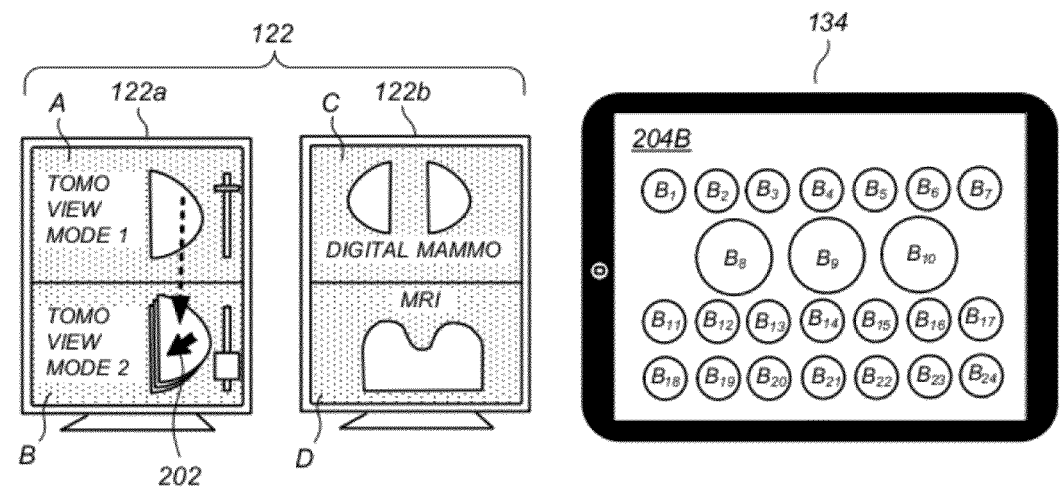
Figure 2C:
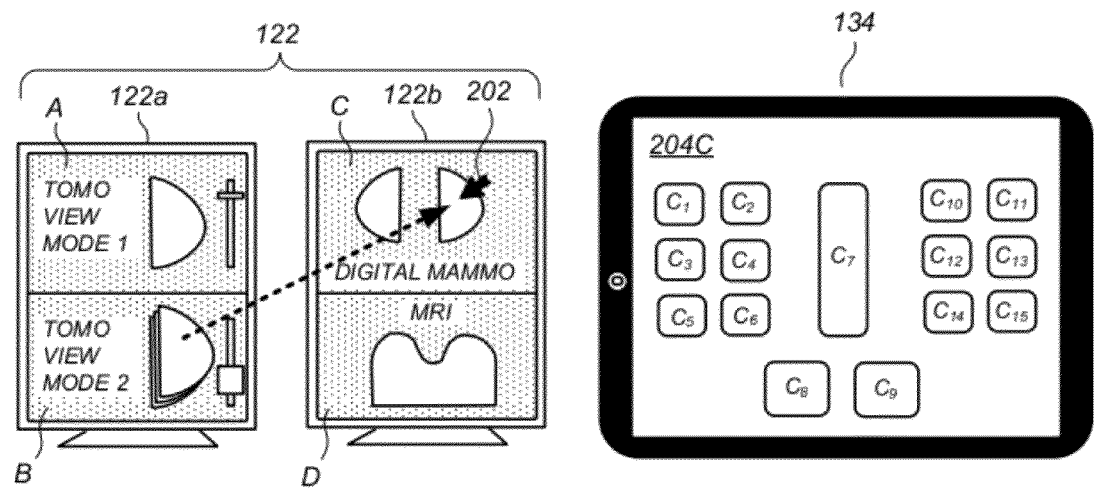
Figure 2D:
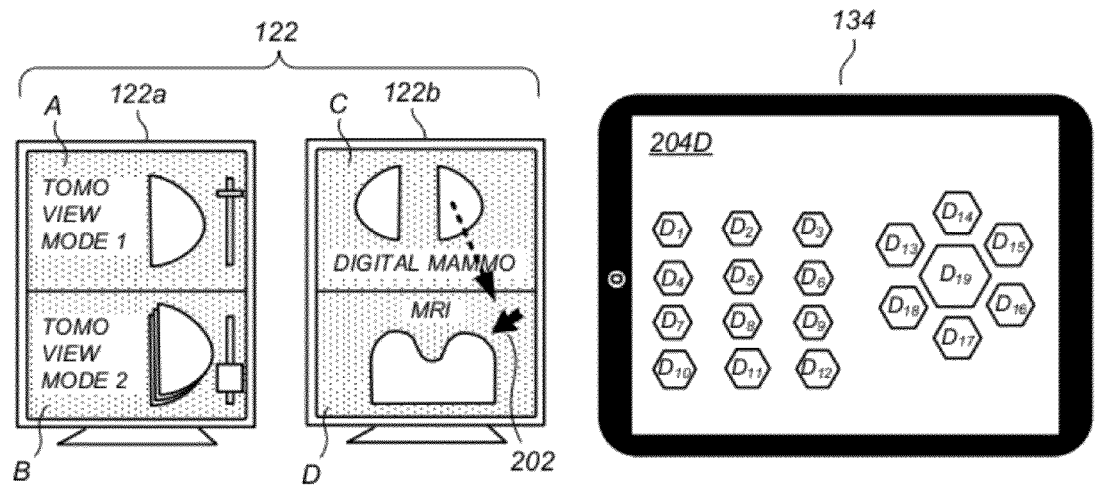

As illustrated in FIG. 2A, when output window "A" is the active output window on the output display 122, this is recognized by the SVTouch host application on the UI processor 126, which then communicates with the SVTouch remote application on the IPAD 134 to invoke a first touchpad control scheme 204A for that type of medical image. The first touchpad control scheme 204A is specially configured to correspond to the particular type, e.g., modality and/or review mode, of the active output window "A", including a variety of visible touchpad controls A1-A24 as shown. In this manner, the UI elements and controls provided thereby of the review workstation 120 are transformed into touchpad or touchscreen elements or controls for that medical image type to provide the same or similar controls with a different arrangement of touchscreen UI elements presented on an IPAD 134.

As used herein, the terms "interface element," "touchscreen element" and "touchpad control" refer to any actuable user control input provided by the IPAD 134, and can include visible touchpad controls and non-visible touchpad controls. As used herein, a visible touchpad control is one that is evidenced by a viewable image of a touchpad key, knob, roller, slider, toggle switch, trackball, or the like that can be actuated at its displayed location on the touchscreen by a "virtual" pressing, turning, sliding, rolling, etc. on the touchpad. The visible touchpad controls A1-A6 can be simple softbuttons, for example, while visible touchpad control A24 can be a slider control, for example. As used herein, non-visible touchpad controls are ones that do not have a particular location identified on the screen, but that are actuable by a user behavior, such as a single-finger linear swipe, double-finger linear swipe, circular swipe, double-finger separation swipe, and so forth.

According to a preferred embodiment, the SVTouch host application on the UI processor 126 and the SVTouch remote application on the IPAD 134 maintain a real-time communication therebetween, and operate and cooperate such that the IPAD 134 provides a current, up-to-date touchpad control scheme that corresponds in real time to the currently active output window on the output display 122. Thus, when the cursor is moved to output window "B", a second touchpad control scheme 204B for that type of image is provided. When the cursor is moved to output window "C", a third touchpad control scheme 204C for that type of image is provided. When the cursor is moved to output window "D", a fourth touchpad control scheme 204D is provided for that type of medical image, and so forth. Advantageously, the user is automatically provided with a control device that is optimized for the particular output window and corresponding type of image upon which they are focusing their attention at that moment. In addition to being advantageous when changing focus from one modality type to another on the user display 122 (e.g., from a tomosynthesis window to an ultrasound window), it can also be advantageous when changing focus from one particular view type to another particular view type within any particular modality (e.g., from a tomosynthesis projection-view window to a tomosynthesis reconstructed slice-view window), because the touchpad control scheme can be optimized and streamlined for each particular type of viewing mode. Thus, the SVTouch host and remote applications according to the preferred embodiments herein are just as advantageous in the context of single-modality review workstations as for multi-modality review workstations.

Generally speaking, at least as a starting point prior to customization, the touchpad controls provided in any particular touchpad control scheme 204A-204D correspond to controls that would be provided by an application specific hardware device, such as the application-specific hardware auxiliary input device 130 shown in FIG. 1, supra. Advantageously, however, a much richer variety of controls, essentially a limitless variety, is made possible. A wide variety of default touch control schemes can be provided in software, hardware, or firmware forms from which the user, or system administrator, can pick and choose at SVTouch setup time. Preferably, the touchpad control schemes can be customized by the user, both (i) in terms of the way any particular control is placed and/or actuated on the IPAD 134 and (ii) in terms of the corresponding function that is achieved in the active output window of the review workstation 120 upon actuation of that control.

Figure 3A:
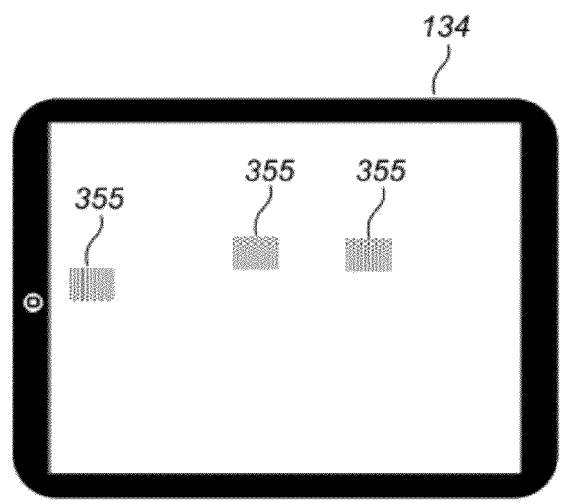
Figure 3B:
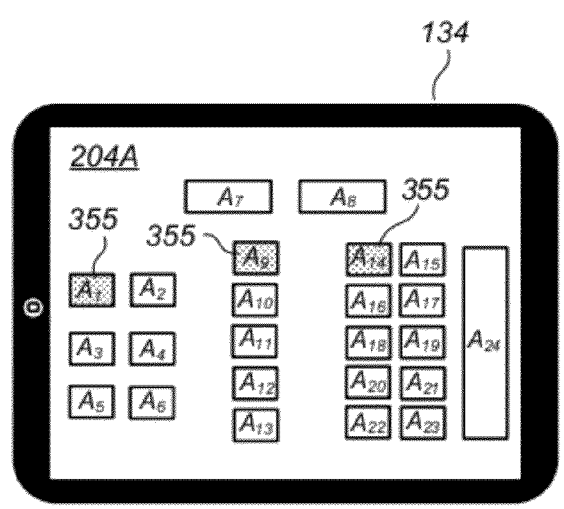

FIGS. 3A-3B illustrate physical modification of an IPAD to further optimize user experience according to a preferred embodiment, wherein textured material patches 355, which are reasonably transparent to light, are physically placed on the touchscreen at locations corresponding to selected "home" touchpad controls. A haptic or tactile feedback sensation is provided when the user places their finger on the "home" touchpad controls, providing similar advantages to the "home" keys (F and J) on a mechanical QWERTY keyboard. The user can then develop a muscle memory (or, alternatively, preserve a muscle memory already developed on another mechanical or electronic input device) for those home keys and the relative locations of the other touchpad controls. The haptic feedback can prevent the need for the user to keep looking at the IPAD 134 (and away from the diagnostic output display 122) to see where the visible touchpad controls are located. The textured material patches 355 can be permanently affixed to the IPAD 134 screen or, more preferably, can be removably affixed thereto (e.g. using adhesives similar to those of POST-IT flags), or affixed to a screen protector or template that is itself removable from the IPAD, or created by making mechanical deformations in a removable screen protector.

Figure 4A:
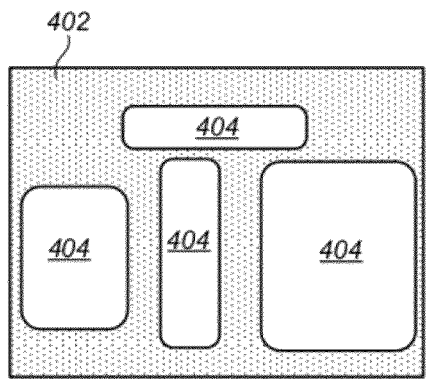
FIGS. 4A-B illustrates different template patterns defining voids in respective spatial arrangements for use in embodiments for providing haptic feedback to a user of a mobile communication device.
Figure 4B:
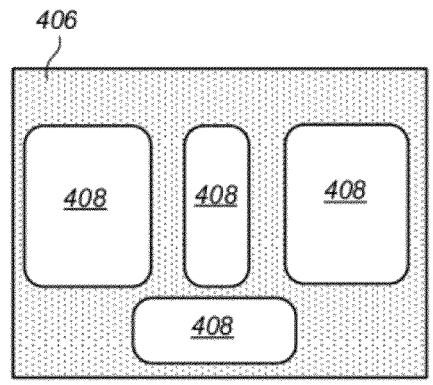
Figure 5A:
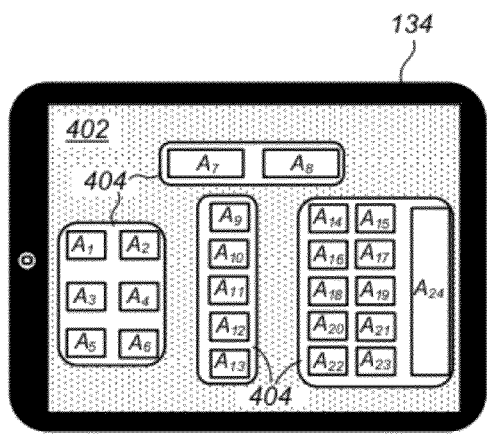
Figure 5B:
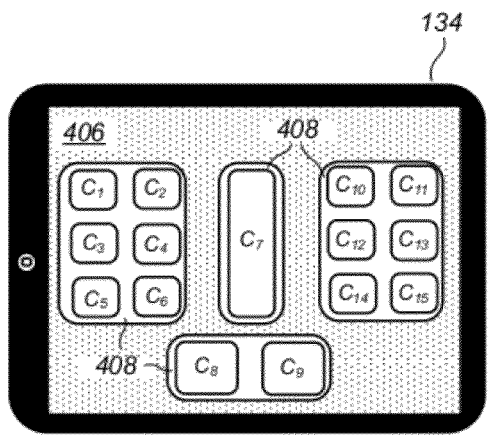

FIG. 4A illustrates a customized template 402 comprising a rigid material, such as PLEXIGLASS, into which void patterns 404 are formed in an arrangement corresponding to the touchscreen control scheme 204A of FIG. 2A, supra. FIG. 4B illustrates a similarly customized template 406 having void patterns 408 corresponding to the touchscreen control scheme 204C of FIG. 2C, supra. FIGS. 5A and 5B illustrate the customized templates 402 and 406 as placed on the IPAD 134 while it is providing touchscreen control schemes 204A and 204C, respectively. The preferred embodiment of FIGS. 4A-5B, which can be used separately from or in conjunction with the preferred embodiment of FIGS. 3A-3B, provides haptic or tactile input to the user hand to guide them to the correct touchpad control locations, thus reducing the need to look at the IPAD 134. Non-rigid materials, such as MYLAR, paper, cardboard, foam, etc., can alternatively be used for the templates 402 and 406. The templates may be permanent or removable depending on the number of "layouts" of touchpad control schemes required.

FIGS. 6A-6D illustrate a hand-specific, location-specific dynamic touchpad control scheme according to a preferred embodiment. As illustrated in FIGS. 6A-6B, the touchpad control scheme 204A is configured such that, when a user taps the IPAD screen with the tips of all five fingers simultaneously, an auxiliary touchpad control scheme 654A is actuated in which a preselected subset of visible touchpad controls 660 (in this example, touchpad controls A6, A22, A3, A14, and A10 for the thumb, index finger, middle finger, ring finger, and little finger, respectively) are automatically and instantaneously placed at the detected locations of the five fingertips.

Additionally, as illustrated in FIGS. 6C-6D, the preselected subset of visible touchpad controls 660 will follow the position of the hand if the user moves the location of their hand. In contradistinction to the one-size-fits-all mechanical device 130 of FIG. 1, the SVTouch system including the customizable selection of the touchpad controls 660 advantageously represents an easy to implement, cost effective solution for allowing a radiologist to customize the control inputs according their own personal proclivities. For example, a first radiologist may have a proclivity to perform a lot of on-screen measurements, and so can select most of the touchpad controls 660 to be measurement tools or to instantiate measurement tools. A second radiologist may have an inclination perform a lot of on-screen magnifications and gamma adjustments, and so can select most of the touchpad controls 660 to be on-screen magnifications and gamma adjustment tools.

In other preferred embodiment (not shown), the auxiliary touchpad scheme 654A is configured to sense a lifting and dropping of the thumb while the other four fingers remain in contact with the screen, whereupon a functionality similar to "ALT" or "SHIFT" on a QWERTY keyboard is provided in which a secondary set of preselected visible touchpad controls automatically replace the preselected subset 660. The user can then lift and drop their thumb again to bring back the original preselected subset 660. Other suitable finger movements to actuate and de-actuate the "SHIFT" functionality can be used without departing from the scope of the present teachings.

Preferably, the operation of the active-window-driven selection of the current touchpad control scheme, as presented in FIGS. 2A-2D supra, continues working in conjunction with the hand-specific, location-specific dynamic touchpad control scheme of FIGS. 6A-6D to adapt to different image types. Thus, for example, if the user has tapped the touchpad at FIG. 6A and the scheme 654A of FIG. 6B is being shown for that image type, and then the active window on the output display 122 is changed from the "A" window of FIG. 2A to the "C" window of FIG. 2C, then the five buttons appearing under the user's fingers in FIG. 6B will automatically change to five preselected "C" buttons (for example, buttons C4, C2, C13, C15, and C10) (not shown) for that image type, or that the user has previously preselected.

Figure 7:
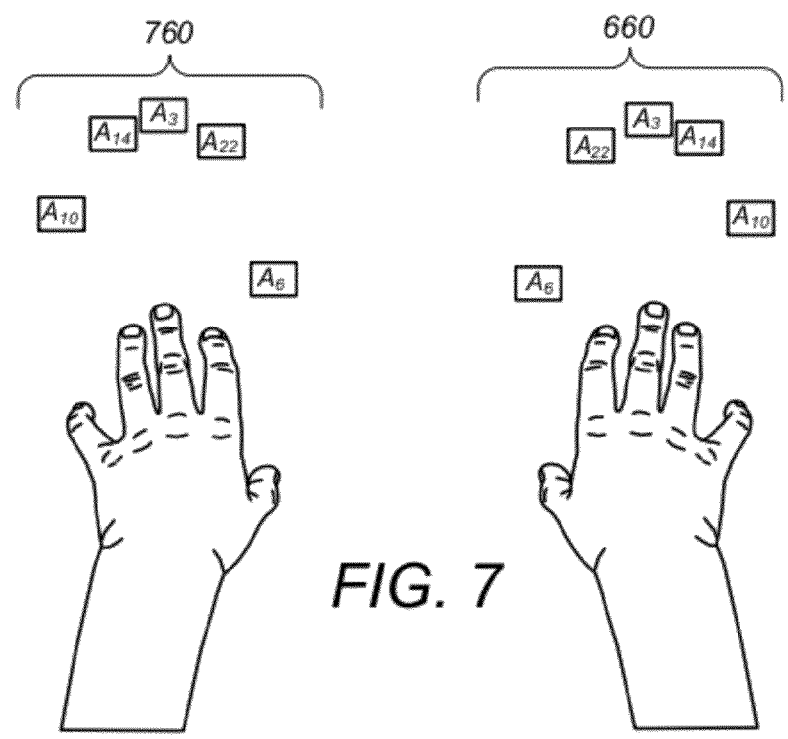
FIG. 7 illustrates how embodiments may be applied to detect a change of hand and to transform or flip a touchscreen interface configured for one hand to a configuration for an opposite hand, wherein in the illustrated embodiment, the touchscreen interface that is flipped is an auxiliary touchscreen user interface.
Figure 8:
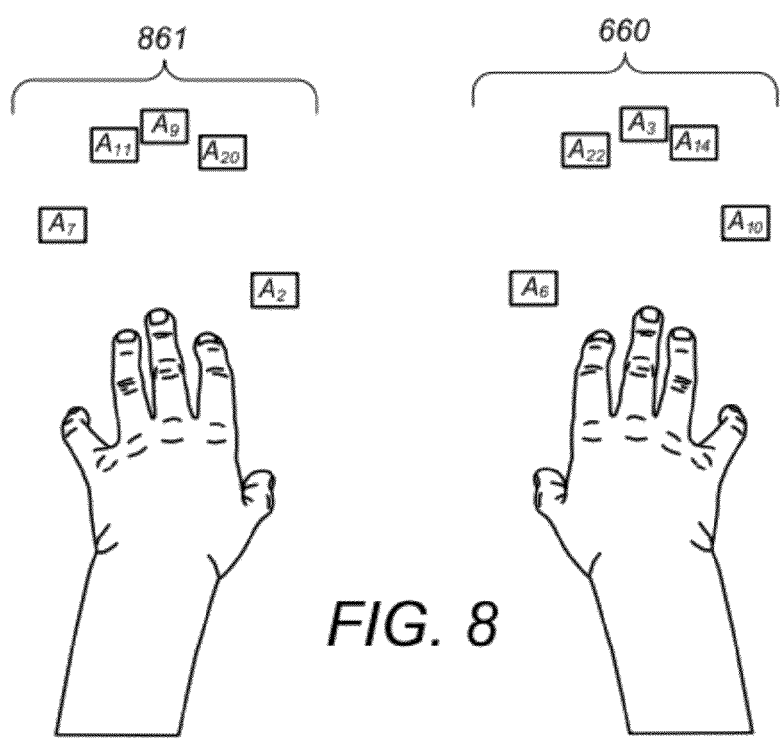
FIG. 8 illustrates how embodiments may be applied to generate a dual-handed touchscreen user interface.

FIGS. 7-8 conceptually illustrate different options for customization and response with respect to different user hands. The SVTouch remote app software is configured to recognize, such as by virtue of fingertip location pattern, whether it is the right hand or the left hand that is touching the touchpad screen. For the option of FIG. 7, the same sets of touchpad controls are used for the opposing hands, but appear in opposing spatial order. For the option of FIG. 8, entirely different subsets of touchpad controls are used for the right and left hands.

FIGS. 9-17 illustrate screen shots of how embodiments may be implemented with regard to active windows corresponding to tomosynthesis and MRI imaging modalities, and associated auxiliary touchscreen interfaces associated with different types of images associated with their respective different imaging modalities.

Figure 9:
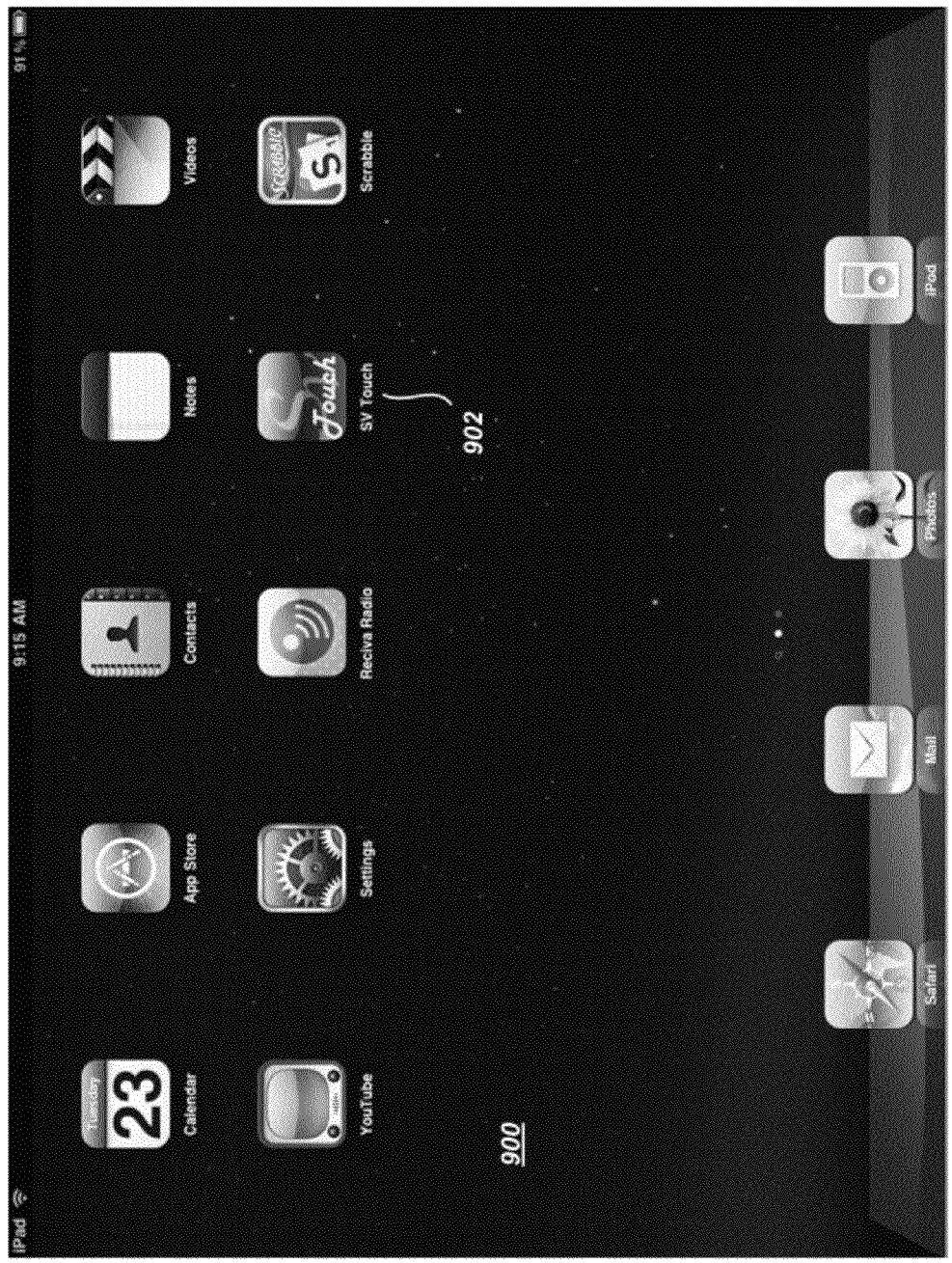
FIG. 9 is a screenshot of a home screen displayed on a mobile communication device screen.

FIG. 9 illustrates a home screen 900 of an IPAD upon which has been loaded the SVTouch remote app, which appears as an SVTouch program icon 902 just like any other application on the IPAD. In one embodiment of commercial operation, the SVTouch app will be downloadable from a website or app store such as Apple's App Store. FIGS. 10-13 and FIG. 16 illustrate screenshots from an IPAD running an SVTouch remote application according to a preferred embodiment, while FIGS. 14-15 and FIGS. 17-18 illustrate screenshots from a processing unit associated with a medical image review workstation that is running an SVTouch host application according to a preferred embodiment.

As made apparent by FIG. 9, the IPAD 134 can belong the user in their personal capacity and can be used for a variety of different purposes or endeavors, such as listening to music, surfing the web, doing online banking, and so forth. The IPAD 134 does not need to have any particular acquisition-related association with any particular medical image review workstation or other aspect of the hospital information system, but rather simply needs to have the SVTouch application loaded onto it, placed in communication with the wireless access point 114, and provided with the IP address of the server that is running the SVTouch host application. Thus, advantageously, the same IPAD used for SVTouch functionality can be used to provide many conveniences and/or comforts for the radiologist as well, such as allowing them to bring music from home, use headphones, make telephone calls, check their e-mail, surf the web, control the ambient room lighting (using an IPAD app), and talk by intercom to other radiologists, technologists, or hospital personnel.

Figure 10:
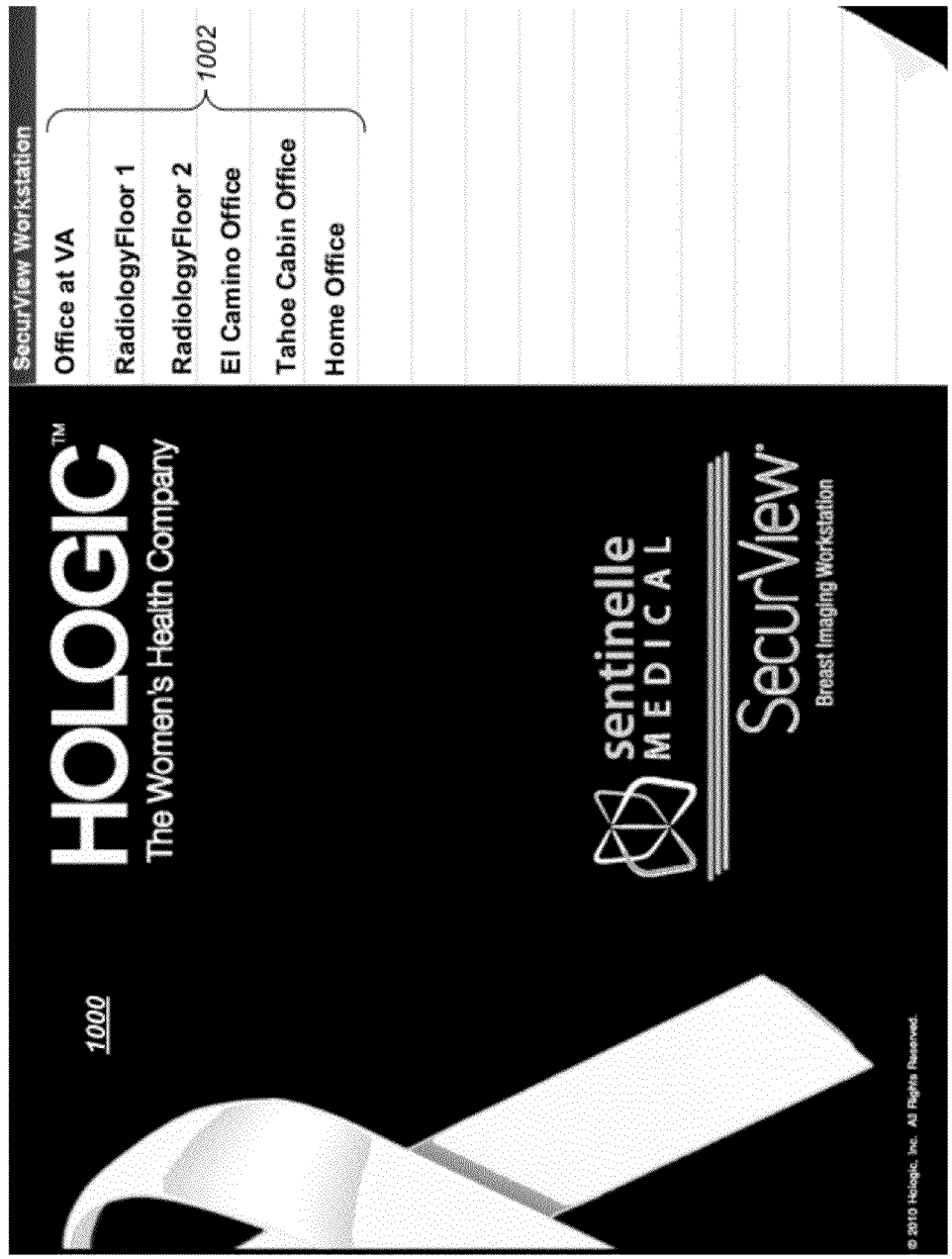
FIG. 10 is a mobile communication device screenshot that follows launching of an application for controlling display of medical images on the mobile communication device according to embodiments.

As illustrated in FIG. 10, upon invoking the SVTouch remote app, the user is presented with an introductory screen 1000 providing a listing 1002 of review workstations having an SVTouch server (SVTouch host) application to which they can connect, which can be one of many different workstations (e.g., their clinic office, their hospital office, their residence or vacation home office, etc.) with which they are associated.

Figure 11:
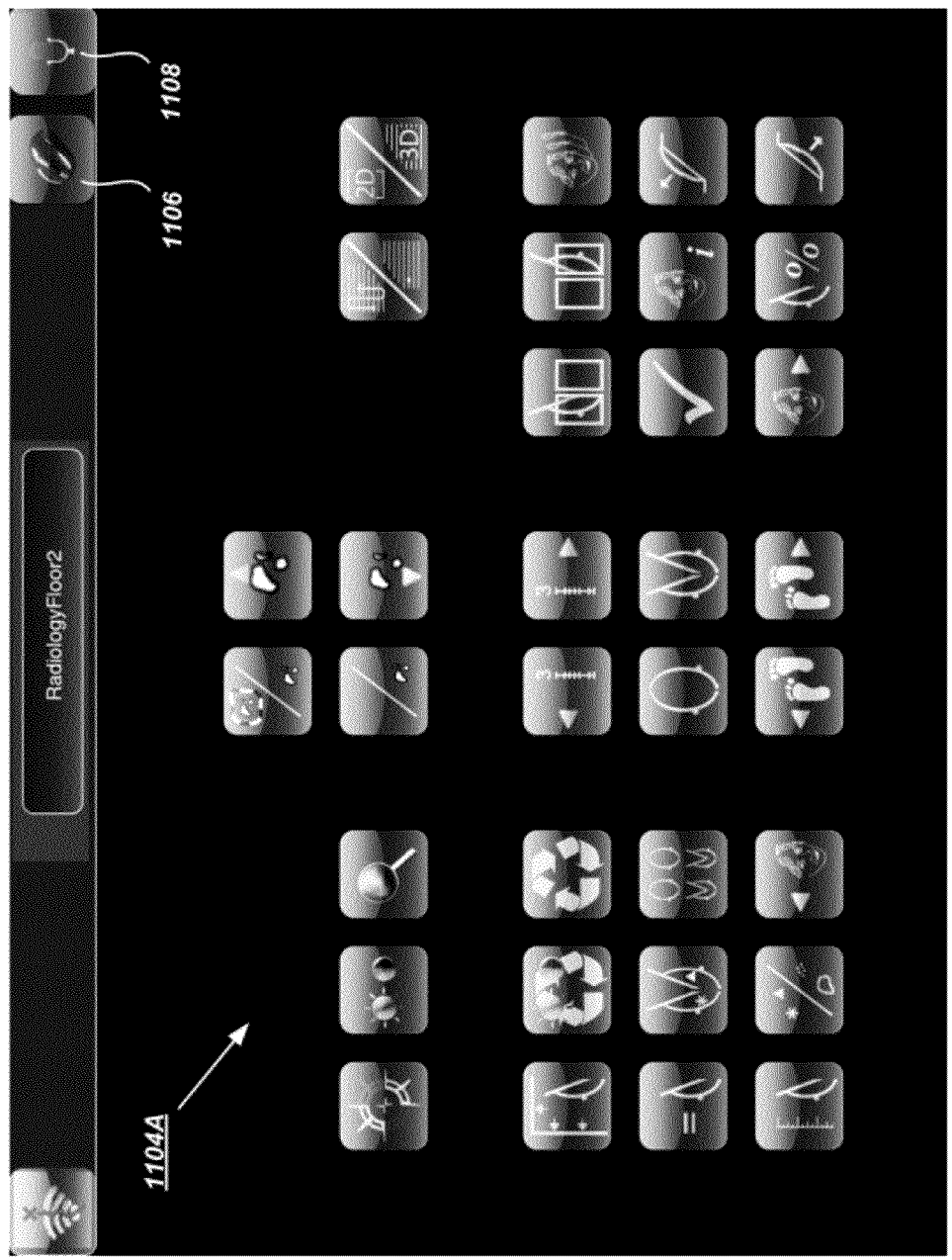
FIG. 11 is a mobile communication device screenshot illustrating an example of a touchscreen user interface generally depicted in FIG. 2A and that is generated and displayed for a first active window corresponding to a tomosynthesis modality.
Figure 12:
FIG. 12 is a mobile communication device screenshot illustrating an example of a touchscreen user interface generally depicted in FIG. 2D and that is generated and displayed for a second active window corresponding to a MRI modality.

FIGS. 11 and 12 illustrated how embodiments can generate different touchscreen interfaces for display on a mobile communication device for different types of images, which may involve one or more of different types of imaging modalities, different view modes, and different images generated by different imaging device manufacturers. FIG. 11 illustrates an example of a touchpad control scheme 1104A for a first type of medical image or an active output window corresponding to an imaging modality type such as a tomosynthesis modality, analogous to the touchpad control scheme 204A of FIG. 2A. FIG. 12 illustrates an example of a touchpad control scheme 1204D for a second type of medical image or a second active output window corresponding to a different imaging modality type such as a MRI modality, analogous to the touchpad control scheme 204D of FIG. 2D. Shown as persistent controls in the upper right hand corner of the touchpad screen are a cursor control toggle 1106 and a microphone on/off toggle 1108. When the cursor control toggle 1106 is set in an active state, the IPAD touchscreen (or, alternatively, some portion of the IPAD touchscreen) becomes operative as a regular touchpad mouse for controlling the cursor 202 (see FIGS. 2A-2D) on the workstation display 122 to select a different window or type of image. When the cursor control toggle 1106 is returned to an inactive state, the IPAD is returned to a mode in which the SVTouch functionalities described herein are resumed.

Figure 13:
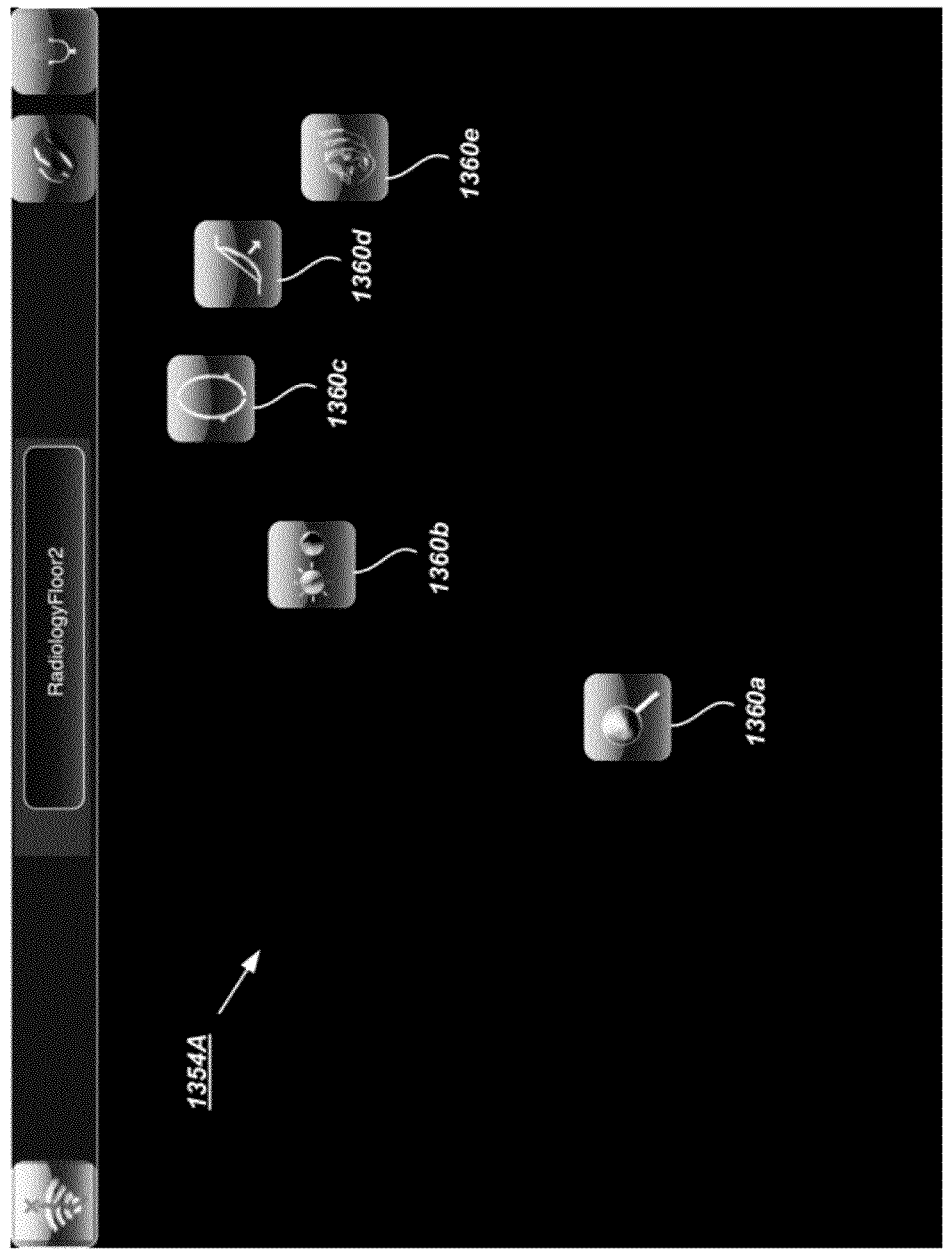
FIG. 13 is a screenshot of an auxiliary touchscreen interface generated according to embodiments and resulting from the user performing a multi-finger tap on the screen of the mobile communication device while the touchscreen interface for the first active window corresponding to a tomosynthesis modality as shown in FIG. 11 was displayed.

FIG. 13 illustrates an auxiliary touchpad control scheme 1354A that appears upon tapping the touchpad control scheme of FIG. 11 (tomosynthesis) with all five right-hand fingers simultaneously, analogous to the functionality described in FIGS. 6A-6D above, and featuring the five visible touchpad controls 1360a-1360e as shown for a particular image type.

Figure 14:
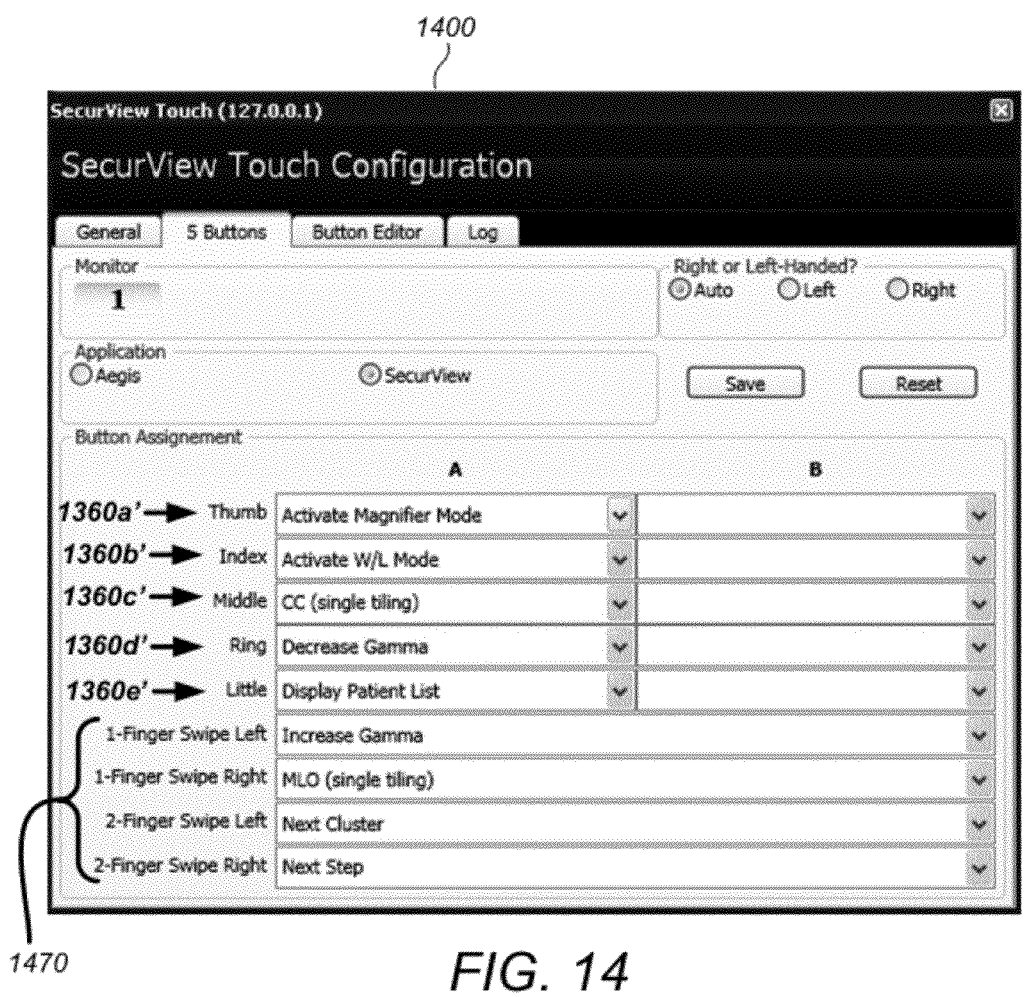
FIG. 14 is a screenshot of a selection or confirmation window that allows a user to assign display controls or functions to elements of the auxiliary touchscreen interface which in the illustrated example includes five interface elements as shown in FIG. 13.
Figure 15:
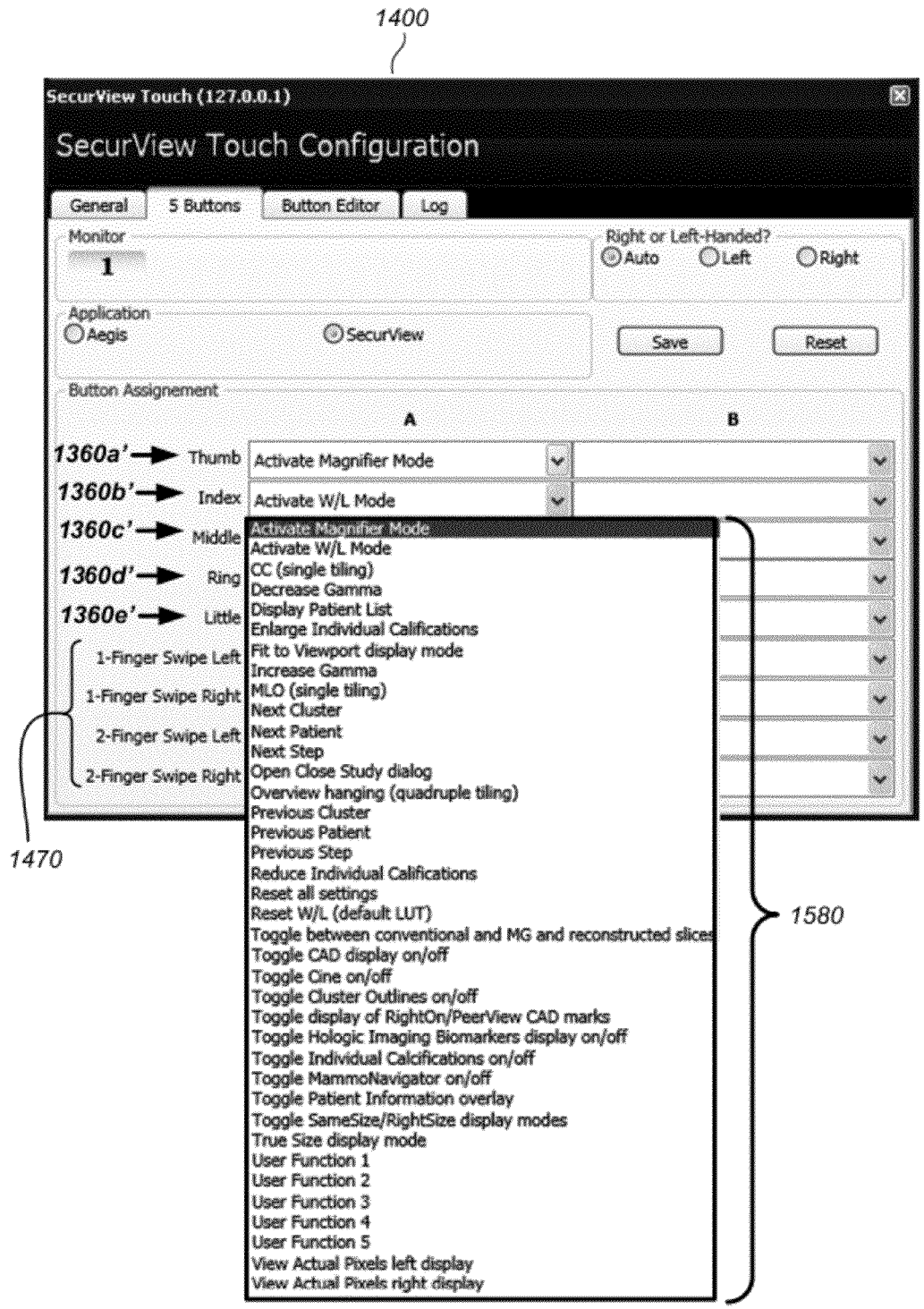
FIG. 15 is a screenshot of an expanded selection or configuration window illustrating in further detail display controls or functions that can be assigned to an element of an auxiliary touchscreen interface as shown in FIGS. 13-14.

FIGS. 14-15 illustrate a 5 button configuration window of the SVTouch host application for selecting the five "favorite" touchpad controls that will appear in FIG. 13. As illustrated, a set of touchpad control selection windows 1360a'-1360e' are provided for allowing the user to choose the functionalities associated with the visible touchpad controls 1360a-1360e, respectively, of FIG. 13.

Also provided are a set of selection windows 1470 for allowing the user to choose the functionalities associated with the non-visible touchpad controls, including a 1-finger swipe left, 1-finger swipe right, 2-finger swipe left, and 2-finger swipe right. Shown in FIG. 15 is one of the selection windows expanded to show a listing 1580 of tomosynthesis-centric workstation functions from which the user can select to associate with the respective "touchpad controls. The column labeled "A" in FIGS. 14-15 is for designating the primary five favorite touchpad controls, while the column labeled "B" in FIGS. 14-15 is for designating the secondary five favorite touchpad controls that will appear in the "SHIFT" or "ALT" scenario described above (e.g., when the user lifts and drops their thumb while the other four fingers remain in contact with the screen).

Figure 16:
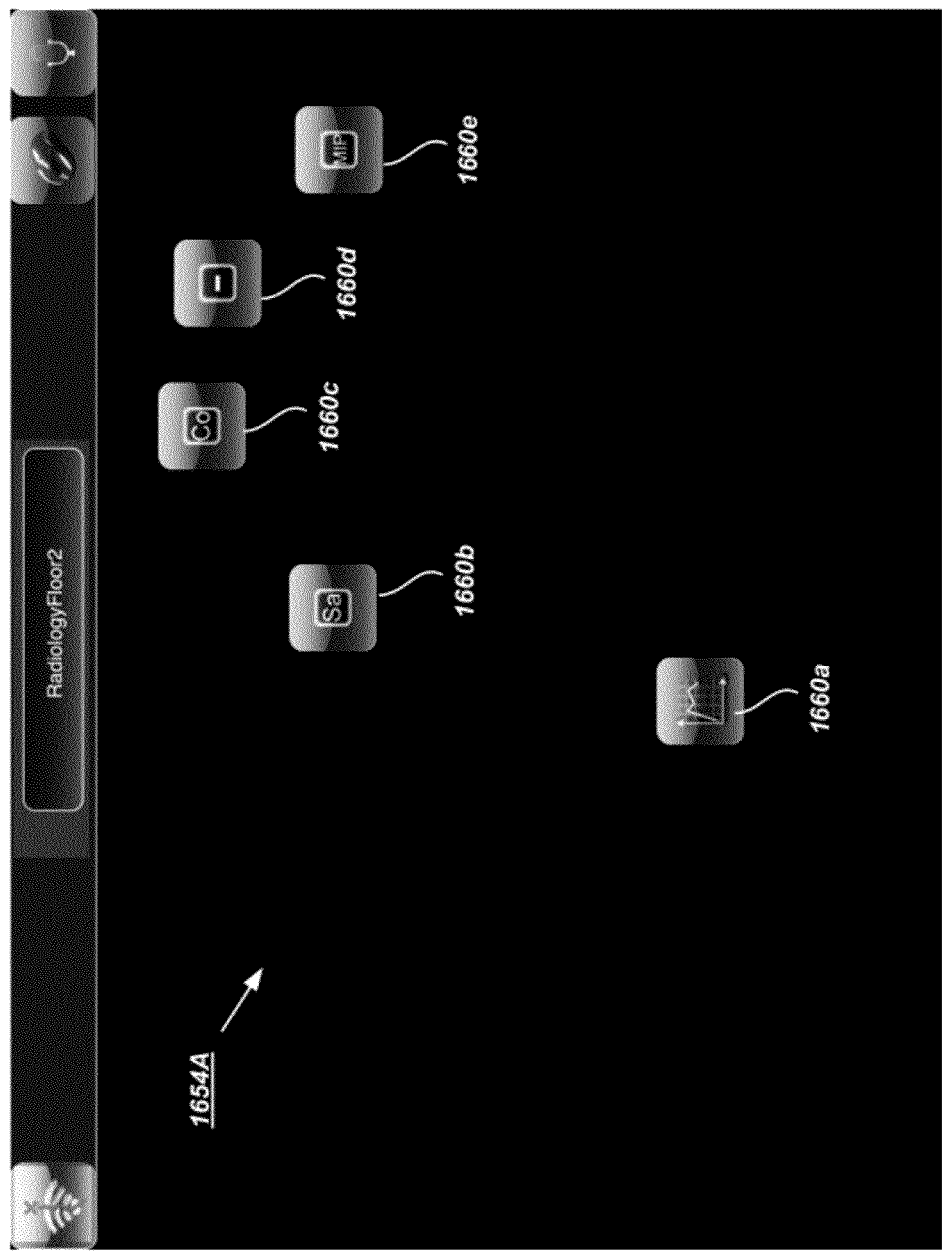
FIG. 16 is a screenshot of an auxiliary touchscreen interface generated according to embodiments and resulting from the user performing a multi-finger tap on the screen of the mobile communication device while the touchscreen interface for the first active window corresponding to a magnetic resonance imaging modality as shown in FIG. 12 was displayed.
Figure 17:
FIG. 17 is a screenshot of a selection or confirmation window that allows a user to assign display controls or functions to elements of the auxiliary touchscreen interface which in the illustrated example includes five interface elements as shown in FIG. 16.
Figure 18:
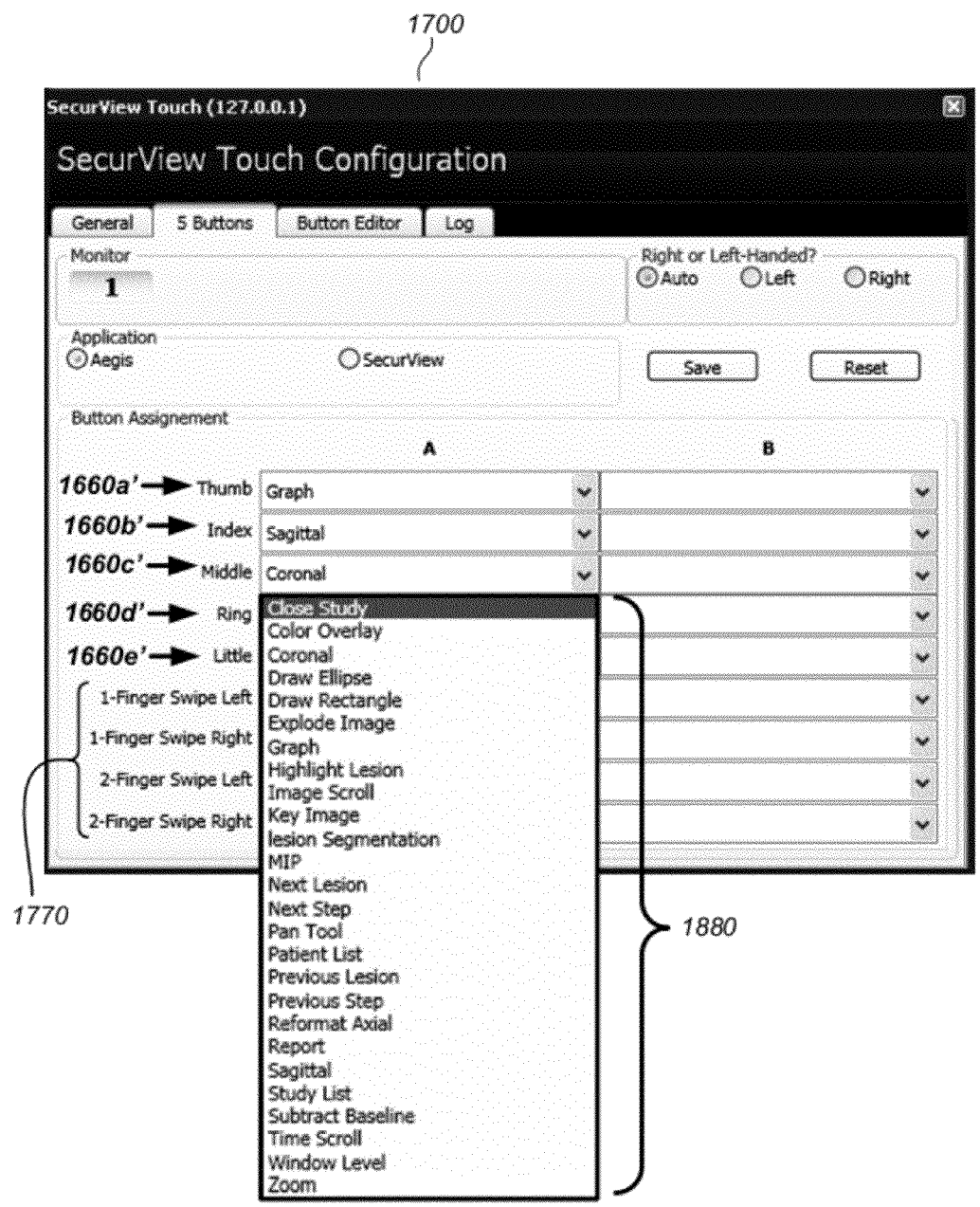
FIG. 18 is a screenshot of an expanded selection or configuration window illustrating in further detail display controls or functions that can be assigned to an element of an auxiliary touchscreen interface as shown in FIGS. 16-17.

FIG. 16 illustrates an auxiliary touchpad control scheme that appears upon tapping the touchpad control scheme of FIG. 12 (MRI) with all five right-hand fingers simultaneously, analogous to the functionality described in FIGS. 6A-6D above, and featuring the five visible touchpad controls 1660a-1660e as shown. FIGS. 17-18 illustrate the 5 button configuration window of the SVTouch host application for selecting the five "favorite" touchpad controls that will appear in FIG. 16. Included in FIGS. 17-18 are a set of touchpad control selection windows 1660a'-1660e' corresponding respectively to the assignments for the visible touchpad controls 1660a-1660e. Further included in FIGS. 17-18 is a set of selection windows 1770 for the non-visible touchpad control functional assignments, and a listing 1880 of MRI-centric workstation functions from which the user can select to associate with the respective touchpad controls.

Notably, although the listings 1580 and 1880 of workstation function from which the user can select in FIG. 15 (tomosynthesis imaging type) and FIG. 18 (MRI imaging type) number in the dozens, there can more generally be hundreds of different review workstation function options provided. Optionally, audio controls ("next CAD mark", "next slab") can be associated with visible or non-visible touchpad controls, such that those commands can be invoked either by the required touch/gesture or by a voice command input. According to one preferred embodiment, a macro language is provided so that touchpad controls can be programmed to invoke specialized routines on the review workstation 120. By way of example, the macro language can provide the ability to specify particular cursor movements (in absolute screen coordinates and/or offset coordinates relative to the currently active window), cursor button clicks, particular keystroke sequences, and so forth.

By way of example, one particular macro can be typed in as the following ASCII sequence: (@100,@300,2){$L1} {#250} {100,450} {$L2} hj. The meaning of this ASCII sequences means: move to absolute position (100,300) on screen 2, then click left mouse button, then wait 250 milliseconds, then move to relative position (100,450), then click the right mouse button, then type the characters "hj".

For one preferred embodiment, a macro recording capability can also be provided that allows the user to record and store particular sequences of mouse movements, keyboard inputs, mouse clicks, and the like, to create a macro without needing to code it in the macro programming language. For one preferred embodiment, the macro programming, recording, and storage methodologies can be similar to those of a popular and easy to use Windows-based macro system called AutoHotKeys, information about which can be found on the World Wide Web at autohotkeys dot com (www.autohotkeys.com).

There is further disclosed the following concepts, which are intrinsically provided as part of the above described technology or which can be readily integrated therewith or incorporated in conjunction therewith. The IPAD/SVTouch can be used as a UI device for a review workstation such as a Hologic SECUREVIEW DX, optionally to completely replace the SECURVIEW DX workflow keypad, to replace the mouse, the on-screen buttons, and/or to replace even the keyboard (since the IPAD on-screen keyboard is available.) The IPAD/SVTouch can be placed into an adjustable orientation for best use as a touch-screen controller, with a balance of ergonomics with visibility of the screen at the most common viewing angles. Soft wrist supports can be provided with the IPAD/SVTouch, and registered indents or touch tape used to allow the user to find a "home" position akin to the little nubs on QWERTY keyboard F and J keys. The IPAD/SVTouch can be customized by touching each finger to the IPAD to determine the length of fingers' reach, optionally to scale the location of control buttons to the length of reach, optionally to scale the size of control buttons according to length of reach, and optionally to scale the length of sliders. Seamless left hand versus right hand control can be provided, such as by optionally auto-flipping the presentation of visible touchscreen controls when the hand is changed.

Optionally, various functions of the administrative display 124 of FIG. 1 can be incorporated onto the IPAD/SVTouch display, such as the patient worklist, or optionally all of the non-imaging administration-type information can be displayed on the IPAD/SVTouch such that all the other screens are used exclusively for imaging information. The IPAD/SVTouch can be used to display RIS information, user documentation, and training materials. Tabbed controls can be provided for access to the keypad/RIS/worklist/reporting system.

Optionally, a non-diagnostic quality miniaturized version of a medical image with CAD markers located thereon can be displayed on the IPAD/SVTouch (i.e., an annotation road map), and the CAD markers can be checked off by touching them at their locations on the touchscreen. The IPAD/SVTouch can be used as a UI for clinical studies, the touch screen for recording finding locations on low-resolution images.

The IPAD/SVTouch can be used to replace existing keypad controls and to provide new controls for displaying and viewing different types of medical images. For binary controls, the assignment of any SECURVIEW function to an IPAD button can be provided. The IPAD/SVTouch can use sliders and regional XY touch-sensitive areas for 1D and 2D controls, and optionally facilitate separation of some 2D controls into two 1D controls (such as WW/WC adjustment). The IPAD/SVTouch can use 2D multi-touch to control zooming, 1D multi-touch controls for stretching 1D things like contrast range or brightness range (setting simultaneous upper and lower ranges), slide controls to slide through temporal series of prior studies, multi-touch to control the two ends of cutplanes in reconstructed MR (and other) images in 3D data sets, and drag and drop controls (e.g., drag from a navigator on the IPAD to window icons on the IPAD rather than, or in addition to, moving the mouse on the workstation display screen). The IPAD/SVTouch can incorporate connections to SECURVIEW DX such as wired USB for direct control, and wireless (802.11a/b/g/n) for wireless control, and wireless (BLUETOOTH) for proximity control (the ability to walk up to the SECURVIEW with an IPAD 134 and it connects automatically). That way doctors can bring their own IPAD/SVTouch and configure them to work with any appropriately equipped SECURVIEW DX.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims, and many alterations and modifications of the present invention will no doubt become apparent to a person of ordinary skill in the art after having read the foregoing description. Thus, it is to be understood that the particular embodiments shown and described by way of illustration are in no way intended to be considered limiting.

For example, while SVTouch remote app configuration associated with FIG. 1 is described as being placed in communication with the wireless access point 114 and being provided with the IP address of the server that is running the SVTouch host application, in other embodiments there can be provided automated or semi-automated proximity-sensing functionality, wherein the IPAD 134 can automatically recognize that it is next to a review workstation, using BLUETOOTH or infrared communications, for example, and can automatically connect to that review workstation and instantiate an SVTouch control session. By way of further example, non-visible touchpad controls that can be incorporated into the IPAD/SVTouch can include a gesture-based language, similar to the Graffiti single-stroke shorthand handwriting recognition system used in personal digital assistant devices based on the PALM OS.

By way of still further example, it is to be appreciated that the functions of the SVTouch host (also called SVTouch server) program can be segregated and placed on different pieces of computing equipment. For example, there can be provided a centralized SVTouch registration and customization service run on a single computer in a HIS/RIS network, and this central server can feed the required information to the SVTouch host and remote apps at the beginning of each radiology review session. Alternatively, there can be a web-based SVTouch registration and customization service hosted by an ASP (application service provider) so that individual hospital IT departments do not need to worry about providing it, or other cloud-based or cloud-like implementation can be provided.

By way of even further example, within the scope of the preferred embodiments is to harness the accelerometer function of the IPAD to assist guiding the workflow. For example, the user can shake the IPAD to select a random patient from the unread patient worklist to read next, jiggle the IPAD to the left to return to the previous patient, jiggle the IPAD to the right to proceed to the next patient, and so on.

By way of still further example, it is to be appreciated that the multiple output windows A-D with different types of images as shown in FIGS. 2A-2D supra can further be differentiated based on system component manufacturer in addition to modality type and review mode type. Thus, for example, the review workstation 120 could be provided with the ability to run review workstation packages from two different manufacturers (e.g., GE and Hologic), with the user being able to display one output window from Hologic and another output window from GE, both windows being of the same modality (such as conventional mammography) and of a similar review modes (such as single-view CC images). In such case, the IPAD/SVTouch would be configured to present a first touchpad control scheme optimized for a first type of medical image, e.g., the GE mammo/single view CC window when the GE output window is active, and then a second touchpad control scheme optimized for a second type of medical image, e.g., the Hologic mammo/single view CC window when the Hologic output window is active.

As a further example, different imaging devices may generate different medical images of the same imaging modalities, and different UIs at the review workstation for those different imaging devices can be transformed into respective touchscreen UIs for display on a mobile communication device. Thus, a first touchscreen UI may be generated, displayed or invoked for display for a tomosynthesis image generated with a first type of imaging device or a tomosynthesis imaging device of a first manufacturer or vendor, whereas a second touchscreen UI may be generated, displayed or invoked for display for another tomosynthesis image generated with a second type of imaging device or tomosynthesis imaging device of a second manufacturer or vendor.

Therefore, reference to the details of the preferred embodiments are not intended to limit their scope, and it will be understood that review workstation UIs may be transformed into touchscreen UIs generated, displayed and invoked for display for different types of imaging modalities, different types of view modes, different types of imaging modalities and view modes, and images generated using different types of imaging devices, e.g., imaging devices of the different manufacturers, which may be of the same or different imaging modality.

Further, it will be understood that embodiments may be directed to computer-implemented methods, involving and/or performed by a review workstation, interface processor and mobile communication device, systems, and non-transitory computer program products, articles of manufacture or mobile applications, including native and downloadable applications executed on a mobile communication device, and that such programs, instructions or applications may be stored in memory including one or more of cache, RAM, ROM, SRAM, DRAM, RDRAM, EEPROM and other types of volatile or non-volatile memory capable of storing data, and that a processor unit that executes instructions may be or include multiple processors, a single threaded processor, a multi-threaded processor, a multi-core processor, or other type of processor capable of processing data. Method embodiments may also be embodied in, or readable from, a computer-readable medium or carrier, e.g., one or more of the fixed and/or removable data storage data devices and/or data communications devices connected to a computer. Carriers may be, for example, magnetic storage medium, optical storage medium and magneto-optical storage medium. Examples of carriers include, but are not limited to, a floppy diskette, a memory stick or a flash drive, CD-R, CD-RW, CD-ROM, DVD-R, DVD-RW, or other carrier now known or later developed capable of storing data. The processor executes program instructions within memory and/or embodied on the carrier to implement method embodiments. Further, embodiments may reside and execute on a mobile communication device such as a Smartphone, tablet computing device and other mobile communication devices.

Additionally, it will be understood that the interface processor may be a stand-alone component or integrated into a review workstation, and that embodiments may be executed by the host program, by the remote program or application, or by both. Thus, it will be understood that embodiments may involve displaying touchscreen interfaces or invoking or providing touchscreen data to a mobile communication device to be processed and displayed on a screen of the mobile communication device. Thus, a touchscreen interface may be displayed or invoked by display by the mobile communication device and/or interface processor.

Further, while certain embodiments are described with reference to a "five finger tap" embodiments may involve other numbers of fingers (defined to include fingers and thumb) simultaneously tapping an IPAD screen. Further, such tap functions may be utilized to display or invoke an auxiliary display and/or other functions such as switching to a different patient. Moreover, the subset of interface elements displayed upon detecting a multi-finger tap may be selected by the user or be selected or identified (e.g., by the host or remote program or application) based at least in part upon interface elements determined to be the most popular or utilized most often and elements positioned under fingers that tapped the screen.

For example, a multi-finger tap with fingers arranged over a first set of keys would result in a subset of interface elements including only those tapped interface elements, whereas a multi-finger tap with fingers arranged over a second, different set of keys would result in a subset of interface elements including only those tapped interface elements. It will also be understood that different subsets of UI elements displayed in response to an action such as a 5 finger tap can be displayed or invoked for display depending on the type of the currently displayed image, such that the subset of interface elements are adapted to and suitable for the particular image type being displayed before the action occurs.

Additionally, while certain embodiments are described with reference to touchscreen interfaces, review modes and imaging modalities associated with breast tissue, it will be understood that embodiments may apply to medical imaging of various other parts of the human body.

Certain embodiments are described with reference to medical images being selected by a user, but medical images may also be automatically selected, e.g., based on a sequence or alphabetical listing.

While this specification describes certain embodiments individually, embodiments may also involve various combinations of features, for example, a combination displaying or invoking for display touchscreen interfaces in combination with one or more or all of the "five finger tap" functionality, selection of an image or active window using the review workstation or mobile communication device, patches or templates to provide haptic feedback, macro execution, customizing location of interface elements displayed according to the positioning and length of a user's fingers, translating or flipping touchscreen interfaces for use by different hands, generating a single handed or dual handed touchscreen interface on a mobile communication device, detecting shaking or jiggling to invoke some action such as switching from reviewing images of one patient to reviewing medical images of another patient, and allowing for control of review of images generated by different review workstation manufacturers using a mobile communication device. Thus, embodiments may involve any one of these or other embodiments or aspects thereof individually or in combination, and description of an embodiment or feature thereof individually is not intended to limit the scope of combinations of such embodiments or features.

Moreover, where computer-implemented methods and associated user actions are described in a particular sequence to indicate certain events occurring in certain order, those of ordinary skill in the art having the benefit of this disclosure would recognize that the ordering may be modified and that such modifications are in accordance with the variations of the invention. Additionally, parts of methods may be performed concurrently in a parallel process when possible, as well as performed sequentially.

What is claimed is:

1. A computer-implemented method for controlling display of medical images, the method comprising:
    displaying or invoking for display, on a screen of a mobile communication device of a user, a first touchscreen interface for controlling display of a selected medical image, the first touchscreen interface comprising a plurality of interface elements;
    detecting the user tapping the screen with a plurality of fingers simultaneously;
    displaying or invoking for display, on the screen, a second touchscreen interface for controlling display of the selected medical image, the second touchscreen interface consisting of a subset of the plurality of the interface elements of the first touchscreen interface;
    determining a second medical image selected by the user;
    determining a third touchscreen interface different than the second touchscreen interface for controlling display of the second medical image;
    displaying or invoking for display, on the screen, the third touchscreen interface comprising a plurality of interface elements;
    detecting a further instance of the user tapping the screen with a same or different plurality of fingers simultaneously;

displaying or invoking for display, on the screen, a fourth touchscreen interface for controlling display of the second medical image, the fourth touchscreen interface consisting of a subset of the plurality of the interface elements of the third touchscreen interface.

2. The computer-implemented method of claim 1, the first medical image and the second medical image being different types of images.

3. The computer-implemented method of claim 2, wherein the first medical image was generated with a first type of imaging modality different than a second type of imaging modality utilized to generate the second medical image.

4. The computer-implemented method of claim 2, wherein the first medical image is displayed in a first type of view mode different than a second type of view mode in which the second medical image is displayed.

5. A computer-implemented method for controlling display of medical images the method comprising:
    displaying or invoking for display, on a screen of a mobile communication device of a user, a first touchscreen interface for controlling display of a selected medical image, the first touchscreen interface comprising a plurality of interface elements;
    detecting the user tapping the screen with a plurality of fingers simultaneously;
    displaying or invoking for display, on the screen, a second touchscreen interface for controlling display of the selected medical image, the second touchscreen interface consisting of subset of the plurality of the interface elements of the first touchscreen interface;
    detecting adjustment of a position of a finger of the user from a first finger position to a second finger position while one or more other fingers of the user remain in contact with the screen; and
    displaying or invoking for display on the screen a third touchscreen interface for control of display of the first medical image in response to detecting the finger position adjustment.

6. The computer-implemented method of claim 5, wherein the finger of the user comprises a pre-determined finger.

7. The computer-implemented method of claim 5, wherein the finger of the user comprises a thumb.

8. The computer-implemented method of claim 5, wherein the second finger position comprises the finger having been lifted upwardly from the screen.

9. The computer-implemented method of claim 5, further comprising:
    detecting adjustment of the finger position from the second finger position back to the first finger position; and
    displaying, or invoking for display, the second touchscreen interface in response to detecting that the finger returned to the first finger position.

10. The computer-implemented method of claim 5, the subset of interface elements consisting of a number of interface elements equal to a detected number of fingers that tapped the screen simultaneously.

11. The computer-implemented method of claim 5, the subset of interface elements being selected by the user such that pre-determined selected interface elements are displayed or invoked for display in response to detecting the user tapping the screen with the plurality of fingers simultaneously.

* * * * *